(12) United States Patent
Eriksson et al.

(10) Patent No.: US 6,399,344 B1
(45) Date of Patent: Jun. 4, 2002

(54) ISOLATED PROTEINS HAVING RETINOL DEHYDROGENASE ACTIVITY, AND WHICH ASSOCIATE WITH RETINOL BINDING RECEPTORS

(75) Inventors: Ulf Eriksson; Andras Simon; Anna Romert, all of Stockholm (SE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 08/937,993

(22) Filed: Sep. 26, 1997

Related U.S. Application Data

(63) Continuation-in-part of application No. 08/729,594, filed on Oct. 11, 1996, which is a continuation-in-part of application No. 08/562,114, filed on Nov. 22, 1995, now Pat. No. 5,972,646, which is a continuation-in-part of application No. 08/375,962, filed on Jan. 20, 1995, now Pat. No. 5,731,195, which is a continuation-in-part of application No. 08/258,418, filed on Jun. 10, 1994, now abandoned.

(51) Int. Cl.$^7$ .............................. C12N 9/04; C12N 9/02; C12N 9/00
(52) U.S. Cl. ..................... 435/190; 435/189; 435/183; 530/350
(58) Field of Search ................................ 530/350, 183, 530/189, 190; 424/94.1, 94.4

(56) References Cited

FOREIGN PATENT DOCUMENTS

| WO | WO9534580 | 12/1995 |
| WO | WO9719167 | 5/1997 |

OTHER PUBLICATIONS

Simon et al. (1996) Genomics 36: 424–430, Sep., 1996.*
Chai et al., "Cloning of a cDNA for a Second Retinol Dehydrogenase Type II", J. Biol. Chem. 270 (47) : 28408–28412 (Nov. 1995).
Suzuki et al., "Identification and Immunohistochemistry of Retinol Dehydrogenase From Bovine Retinol Pigment Epithelium", Biochim et Biophys. Acta 1163: 201–208 (1993).
Ishiguro et al., "Purification of Retinol Dehydrogenase From Bovine Retinal Rod Outer Segments", Biol. Chem. 266(23) : 15520–15524 (1991).
Bavik et al., "Identification and Partial Characterization of a Retinal Pigment Epithelial Membrane Receptor for Plasma Retinol–binding Protein", J. Biol. Chem. 266(23) : 14978–14985 (1991).
Duester et al., "Molecular cloning and characterization of a cDNA for the β subunit of human alcohol dehydrogenase", Proc. Natl. Acad. Sci. USA 81: 4055–4059 (1984).
Chai et al., "Cloning of a cDNA for Liver Microsomal Retinol Dehydrogenase", J. Biol. Chem. 270 (8) : 3900–3094 (Feb. 24, 1995).
Chai et al., "Cloning of a rat cDNA encoding retinol dehydrogenase isozyme type III", Gene 169: 219–222 (1996).
Simon et al., "The retinol Pigment Epithelial–specific 11–cis Retinol Dehydrogenase Belongs to The Family of Short Chain Alcohol Dehydrogenases", J. Biol. Chem. 270 (3) : 1107–1112 (1997).
Mertz et al., "Identification and Characterization of a Stereo–specific Human Enzyme That Catalyzes 9–cis–retinol oxidation", J. Biol. Chem. 272 (12) : 11744–11749 (May 2, 1997).

* cited by examiner

*Primary Examiner*—Michael Pak
(74) *Attorney, Agent, or Firm*—Fulbright & Jaworski L.L.P.

(57) ABSTRACT

Isolated membrane associated proteins which have a molecular weight of from about 30 kD to about 36 kilodaltons as determined by SDS-PAGE, are disclosed. The proteins have cis retinol dehydrogenase activity, such as 9, 11 or 13 cis retinol dehydrogenase activity, or cis activity at more than one position. Other trans-retinol dehydrogenases are also disclosed. Nucleic acid molecules which code for the proteins are also disclosed.

6 Claims, 7 Drawing Sheets

FIG. 3

```
   1                                        AGCTTTCCCCTGAGGAGGTCACCTGGGCTCCAGCC

Met Trp Leu Pro Leu Leu Leu Gly Val Leu Leu Trp Ala Ala Leu Trp Leu   17
  36    ATG TGG CTG CCT CTG CTG CTG GGT GTC TTG CTC TGG GCA GCA CTG TGG TTG

Leu Arg Asp Arg Gln Cys Leu Pro Ala Ser Asp Ala Phe Ile Phe Ile Thr   34
  88    CTC AGG GAC CGG CAG TGC CTG CCA GCC AGC GAT GCC TTT ATC TTC ATC ACC

Gly Cys Asp Ser Gly Phe Gly Arg Leu Leu Ala Leu Arg Leu Asp Gln Arg   51
 139    GGC TGT GAC TCG GGC TTT GGG CGG CTC CTT GCT CTG AGG CTG GAC CAG AGA

Gly Phe Arg Val Leu Ala Ser Cys Leu Thr Pro Ser Gly Ala Glu Asp Leu   68
 190    GGC TTC CGA GTA CTG GCC AGC TGC CTG ACA CCC TCG GGG GCG GAG GAC CTC

Gln Arg Val Ala Ser Ser Arg Leu His Thr Thr Leu Leu Asp Val Thr Asp   85
 241    CAG CGG GTC GCC TCC TCC CGC CTC CAC ACC ACC CTG CTG CAT GTC ACA GAT

Pro Gln Ser Ile Arg Gln Ala Val Lys Trp Val Glu Thr His Val Gly Glu  102
 292    CCC CAG AGC ATG CGG CAG GCA GTC AAG TGG GTG GAA ACG CAT GTT GGG GAA

Ala Gly Leu Phe Gly Leu Val Asn Asn Ala Gly Val Ala Gly Ile Ile Gly  119
 343    GCA GGG CTT TTT GGT CTG GTG AAT AAT GCT GGT GTG GCT GGC ATC ATT GGT

Pro Thr Pro Trp Gln Thr Arg Glu Asp Phe Gln Arg Val Leu Asn Val Asn  136
 394    CCC ACC CCA TGG CAG ACG CGG GAG GAC TTC CAG CGG GTG CTG AAT GTG AAC

Thr Leu Gly Pro Ile Gly Val Thr Leu Ala Leu Leu Pro Leu Leu Leu Gln  153
 445    ACG CTG GGT CCC ATC GGG GTC ACC CTC GCC CTG CTG CCC CTG CTG CTG CAG

Ala Arg Gly Arg Val Ile Asn Ile Thr Ser Val Leu Gly Arg Leu Ala Ala  170
 496    GCC CGG GGC CGA GTG ATC AAC ATC ACC AGT GTC CTT GGC CGT CTG GCA GCC

Asn Gly Gly Gly Tyr Cys Val Ser Lys Phe Gly Leu Glu Ala Phe Ser Asp  187
 547    AAT GGA GGG GGC TAC TGC GTC TCC AAG TTT GGC GTC GAG GCC TTC TCT GAC

Ser Leu Arg Arg Asp Val Ala Pro Phe Gly Val Arg Val Ser Ile Val Glu  204
 598    AGC CTG AGG CGA GAT GTG GCT CCT TTT GGG GTA CGG GTC TCT ATC GTG GAA

Pro Gly Phe Phe Arg Thr Pro Val Thr Asn Leu Glu Thr Leu Glu Asp Thr  221
 649    CCT GGC TTC TTC CGA ACC CCT GTG ACA AAC CTG GAA ACT TTG GAG GAC ACC

Leu Gln Ala Cys Trp Ala Arg Leu Pro Pro Ala Thr Gln Ala Leu Tyr Gly  238
 700    CTG CAG GCC TGC TGG GCA CGG CTG CCT CCA GCC ACA CAG GCC CTC TAT GGG

Glu Ala Phe Leu Thr Lys Tyr Leu Arg Val Gln Gln Arg Ile Met Asn Met  255
 751    GAG GCC TTC CTC ACC AAA TAC CTG AGA GTG CAG CAA CGT ATC ATG AAC ATG

Ile Cys Asp Pro Asp Leu Ala Lys Val Ser Arg Cys Leu Glu His Ala Leu  272
 802    ATC TGT GAT CCG GAC CTG GCC AAG GTG AGC AGG TGC CTG GAG CAT GCC CTA

Thr Ala Arg His Pro Arg Thr Arg Tyr Ser Pro Gly Trp Asp Ala Lys Leu  289
 853    ACT GCC CGT CAC CCC AGA ACC CGC TAC AGC CCA GGC TGG GAT GCC AAG CTG

Leu Trp Leu Pro Ala Ser Tyr Leu Pro Ala Arg Leu Val Asp Ala Val Leu  306
 904    CTC TGG TTG CCA GCC TCC TAC TTG CCA GCC AGG CTG GTG GAT GCT GTG CTC

Ala Trp Val Leu Pro Lys Pro Ala Gln Thr Val Tyr Stop                 318
 955    GCC TGG GTC CTT CCC AAG CCT GCC CAG ACA GTC TAC TAA ATCCAGCCCTCCAGC

1009    AAAAGATGGTTGTTCAAGGCAAGGACTCTGATTTATTCTGTCCCCTACCCTGGTACTGCCTGGTGTG

1076    TGGCATAAAACAGTCACTCAATAAATGTATTATTCAAAACAAAAAAAA
```

FIG. 4

```
            1                                                                50
    p32     ..........  ..........  ........MW  LPLLLGVLLW  AALWLLRDRQ
    BDH     MMLAARLSRP  LSQLPGKALS  VCDRENGTRH  TLLFYPASFS  PDTRRTYTSQ
    FABG    ..........  ..........  ..........  ..........  ..........
    EDH     ..........  ..........  ..........  ..........  ..........

51                                                               100
    p32     CLPASDAFIF  ITGCDSGFGR  LLALRLD...  QRGFRVLASC  L....TP...
    BDH     ADAASGKAVL  VTGCDSGFGF  SLAKHLH...  SKGFLVFAGC  LLKEQGD...
    FABG    .MNFEGKIAL  VTGASRGIGR  AIAETLA...  ARGGKVIGTA  ....TSE...
    EDH     ....ARTVVL  ITGCSSGIGL  HLAVRLASDP  SQSFKVYATL  RDLKTQGRLW 101                                                              150
    p32     SGAEDLQRVA  SSRLHTTLLD  VTDPQSIRQA  VKWVETHV..  GEAGLFGLVN
    BDH     AGVRELDSLK  SDRLRTIQLN  VCNSEEVEKA  VETVRSGLKD  PEKGMWGLVN
    FABG    NGAQAISDYL  GANGKGLMLN  VTDPASTESV  LEKIRAEFGE  VDI....LVN
    EDH     EAARALA.CP  PGSLETLQLD  VRDSKSVAAA  RERVTEGRVD  V......LVC 151                                                              200
    p32     NAGVAGIIGP  TPWQTREDFQ  RVLNVNTLGP  IGVTLALLPL  LLQAR.GRVI
    BDH     NAGIST.FGE  VEFTSMETYK  EVAEVNLWGT  VRTTKSFLPL  LRRAK.GRVV
    FABG    NAGI.TRDNL  LMRMKDEEWN  DIIETNLSSV  FRLSKAVMRA  MMKKRHGRII
    EDH     NAGL.GLLGP  LEALGEDAVA  SVLDVNVVGT  VRMLQAFLPD  MKRRGSGRVL

201              ▽
    P32     NITSVLGRLA  ANG.GGYCVS  KFGLEAFSDS  LRRDVAPFGV  RVSIVEPGFF
    BDH     NISSMLGRMA  NPARSPYCIT  KFGVEAFSDC  LRYEMHPLGV  KVSVVEPGNF
    FABG    TIGSVVGTMG  NGGQANYAAA  KAGLIGFSKS  LAREVASRGI  TVNVVAPGFI
    EDH     VTGSVGGLMG  LPFNDVYCAS  KFALEGLCES  LAVLLLPFGV  HLSLIECGPV 251                                                              300
    p32     ..RT..PV..  TNLETLEDTL  QACWARL...  ..........  PPATQALYGE
    BDH     IAAT..SL..  YSPERIQAIA  KKMWDEL...  ..........  PEVVRKDYGK
    FABG    ETDMTRAL..  SDDQRAGILA  QVPAGRL...  ..........  GGAQEIANAV
    EDH     HTAFMEKVLG  SPEEVLDRTD  IHTFHRFYQY  LAHSKQVFRE  AAQNPEEVAE 301                                                              350
    p32     AFLTKYLRVQ  QRIMNMICDP  DLAKVSRCLE  HALTARHPRT  RYSPGWDAKL
    BDH     KYFDEKIAKM  ETYCN.SGST  DTSSVINAVT  HALTAATPYT  RYHPMDYYWW
    FABG    AFLASDEAAY  ITGETLHVNG  GMYMV.....  ..........  ..........
    EDH     VFLTALRAPK  PTLRYFTTER  FLPLLRMRLD  DPSGSNYVTA  MHREVFGDVP 351                            389
    P32     LWLPA.SYLP  ARLVDAVLAW  VLPKPAQTVY  ..........
    BDH     LRMQVMTHFP  GAISDKIYIH  ..........  ..........
    FABG    ..........  ..........  ..........  ..........
    FDH     AKAEAGAEAG  GGAGPGAEDE  AGRSAVGDPE  LGDPPAAPQ
```

(12) United States Patent US 6,399,344 B1

```
                         SEQUENCE LISTING (1) GENERAL INFORMATION:

(iii) NUMBER OF SEQUENCES:  46

(2) INFORMATION FOR SEQ ID NO: 1:

(i) SEQUENCE CHARACTERISTICS:
         (A) LENGTH: 18 amino acids
         (B) TYPE: amino acid
         (D) TOPOLOGY: linear (ii) MOLECULE TYPE: protein (xi) SEQUENCE DESCRIPTION: SEQ ID NO: 1:

Leu Val Glu Ala Val Leu Ala Glu Val Leu P ro Lys Pro Ala Gln Thr
                 5                  10                  15

Val Ala (2) INFORMATION FOR SEQ ID NO: 2:

(i) SEQUENCE CHARACTERISTICS:
         (A) LENGTH: 8 amino acids
         (B) TYPE: amino acid
         (D) TOPOLOGY: linear (ii) MOLECULE TYPE: protein (xi) SEQUENCE DESCRIPTION: SEQ ID NO: 2:

Tyr Ser Pro Gly Trp Asp Ala Lys
                 5

(2) INFORMATION FOR SEQ ID NO: 3:

(i) SEQUENCE CHARACTERISTICS:
         (A) LENGTH: 15 amino acids
         (B) TYPE: amino acid
         (D) TOPOLOGY: linear (ii) MOLECULE TYPE: protein (xi) SEQUENCE DESCRIPTION: SEQ ID NO: 3:

Thr Pro Val Thr Asn Leu Glu Thr Leu Glu A sp Thr Leu Gln Ala
                 5                  10                  15

(2) INFORMATION FOR SEQ ID NO: 4:

(i) SEQUENCE CHARACTERISTICS:
         (A) LENGTH: 7 amino acids
         (B) TYPE: amino acid
         (D) TOPOLOGY: linear (ii) MOLECULE TYPE: protein (xi) SEQUENCE DESCRIPTION: SEQ ID NO: 4:

Asp Val Ala Pro Phe Gly Val
                 5
```

(2) INFORMATION FOR SEQ ID NO: 5:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 5:

Leu His Thr Thr Leu Leu Asp Val Thr Asp P ro Gln Ser Ile
                  5                 10

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: sin gle
        (D) TOPOLOGY: linear (ii) MOLECULE TYPE: nucleic acid (xi) SEQUENCE DESCRIPTION: SEQ ID NO: 6:

ACGTGAATTC TNGTNGARGC NGT                                        23

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: sin gle
        (D) TOPOLOGY: linear (ii) MOLECULE TYPE: nucleic acid (xi) SEQUENCE DESCRIPTION: SEQ ID NO: 7:

ACGTGAATTC ACNGTYTGNG CNGGYTT                                27

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 8:

ACGTGAATTC CCNGTNACNA AYYT                                     24

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: nucleic acid (xi) SEQUENCE DESCRIPTION: SEQ ID NO: 9:

ACGTGAATTC GCYTGNARNG TRTCYTC                                27

(2) INFORMATION FOR SEQ ID NO: 10:

(i) SEQUENCE CHARACTERISTICS:

(A) LENGTH: 1122 base pairs
        (B) TYPE: nucleic acid
        (C) STRANDEDNESS: sin gle
        (D) TOPOLOGY: linear (ii) MOLECULE TYPE: cDNA (ix) FEATURE:
        (A) NAME/KEY: p32;11-cis retinol dehydrogenase (xi) SEQUENCE DESCRIPTION: SEQ ID NO:10:

```
AGCTTTCCCC TGAGGAGGTC ACCTGGGCTC CAGCC ATG TGG CTG CCT CTG CAG                53
                                      Met Trp Leu Pro Leu Gln
                                                        5

TGC CTG CTG CTG GGT GTC TTG CTC TGG GCA G CA CTG TGG TTG CTC AGG             101
Leu Gly Val Leu Leu Trp Ala Ala Leu Trp L eu Leu Arg Asp Arg Gln
             10                  15                     20

GAC CGG CCA GCC AGC GAT GCC TTT ATC TTC A TC ACC GGC TGT GAC TCG             149
Cys Leu Pro Ala Ser Asp Ala Phe Ile Phe I le Thr Gly Cys Asp Ser
             25                  30                     35

GGC TTT GGG CGG CTC CTT GCT CTG AGG CTG G AC CAG AGA GGC TTC CGA             197
Gly Phe Gly Arg Leu Leu Ala Leu Arg Leu A sp Gln Arg Gly Phe Arg
             40                  45                     50

GTA CTG GCC AGC TGC CTG ACA CCC TCG GGG G CG GAG GAC CTC CAG CGG             245
Val Leu Ala Ser Cys Leu Thr Pro Ser Gly A la Glu Asp Leu Gln Arg
55                60                  65                     70

GTC GCC TCC TCC CGC CTC CAC ACC ACC CTG C TG GAT GTC ACA GAT CCC             293
Val Ala Ser Ser Arg Leu His Thr Thr Leu L eu Asp Val Thr Asp Pro
             75                  80                     85

CAG AGC ATC CGG CAG GCA GTC AAG TGG GTG G AA ACG CAT GTT GGG GAA             341
Gln Ser Ile Arg Gln Ala Val Lys Trp Val G lu Thr His Val Gly Glu
             90                  95                    100

GCA GGG CTT TTT GGT CTG GTG AAT AAT GCT G GT GTG GCT GGC ATC ATT             389
Ala Gly Leu Phe Gly Leu Val Asn Asn Ala G ly Val Ala Gly Ile Ile
            105                 110                    115

GGT CCC ACC CCA TGG CAG ACG CGG GAG GAC T TC CAG CGG GTG CTG AAT             437
Gly Pro Thr Pro Trp Gln Thr Arg Glu Asp P he Gln Arg Val Leu Asn
            120                 125                    130

GTG AAC ACG CTG GGT CCC ATC GGG GTC ACC C TC GCC CTG CTG CCC CTG             485
Val Asn Thr Leu Gly Pro Ile Gly Val Thr L eu Ala Leu Leu Pro Leu
135              140                 145                    150

CTG CTG CAG GCC CGG GGC CGA GTG ATC AAC A TC ACC AGT GTC CTT GGC             533
Leu Leu Gln Ala Arg Gly Arg Val Ile Asn I le Thr Ser Val Leu Gly
             155                 160                    165

CGT CTG GCA GCC AAT GGA GGG GGC TAC TGC G TC TCC AAG TTT GGC CTG             581
Arg Leu Ala Ala Asn Gly Gly Gly Tyr Cys V al Ser Lys Phe Gly Leu
             170                 175                    180

GAG GCC TTC TCT GAC AGC CTG AGG CGA GAT G TG GCT CCT TTT GGG GTA             629
Glu Ala Phe Ser Asp Ser Leu Arg Arg Asp V al Ala Pro Phe Gly Val
             185                 190                    195

CGG GTC TCT ATC GTG GAA CCT GGC TTC TTC C GA ACC CCT GTG ACA AAC             677
Arg Val Ser Ile Val Glu Pro Gly Phe Phe A rg Thr Pro Val Thr Asn
             200                 205                    210

CTG GAA ACT TTG GAG GAC ACC CTG CAG GCC T GC TGG GCA CGG CTG CCT             725
Leu Glu Thr Leu Glu Asp Thr Leu Gln Ala C ys Trp Ala Arg Leu Pro
215              220                 225                    230

CCA GCC ACA CAG GCC CTC TAT GGG GAG GCC T TC CTC ACC AAA TAC CTG             773
Pro Ala Thr Gln Ala Leu Tyr Gly Glu Ala P he Leu Thr Lys Tyr Leu
             235                 240                    245

AGA GTG CAG CAA CGT ATC ATG AAC ATG ATC T GT GAT CCG GAC CTG GCC             821
Arg Val Gln Gln Arg Ile Met Asn Met Ile C ys Asp Pro Asp Leu Ala
             250                 255                    260
```

```
AAG GTG AGC AGG TGC CTG GAG CAT GCC CTA A CT GCC CGT CAC CCC AGA      869
Lys Val Ser Arg Cys Leu Glu His Ala Leu T hr Ala Arg His Pro Arg
            265                 270                 275

ACC CGC TAC AGC CCA GGC TGG GAT GCC AAG C TG CTC TGG TTG CCA GCC      917
Thr Arg Tyr Ser Pro Gly Trp Asp Ala Lys L eu Leu Trp Leu Pro Ala
            280                 285                 290

TCC TAC TTG CCA GCC AGG CTG GTG GAT GCT G TG CTC GCC TGG GTC CTT      965
Ser Tyr Leu Pro Ala Arg Leu Val Asp Ala V al Leu Ala Trp Val Leu
295             300                 305                 310

CCC AAG CCT GCC CAG ACA GTC TAC TAA ATCCAGCC CT CCAGCAAAG            1012
Pro Lys Pro Ala Gln Thr Val Tyr
                315

ATGGTTGTTC AAGGCAAGGA CTCTGATTTA TTCTGTCCCC TACCCTGGTA C TGCCTGGTG  1072

TGTGGCATAA AACAGTCACT CAATAAATGT ATTATTCAAA ACAAAAAAAA              1122

(2) INFORMATION FOR SEQ ID NO: 11:

(i) SEQUENCE CHARACTERISTICS:
        (A) LENGTH: 344 amino acids
        (B) TYPE: amino acid
        (D) TOPOLOGY: linear (ii) MOLECULE TYPE: protein (ix) FEATURE:
        (A) NAME/KEY: Rat D-b- hydroxybutyrate dehydrogenase (rBDH)

(xi) SEQUENCE DESCRIPTION: SEQ ID NO:11:

Met Met Leu Ala Ala Arg Leu Ser Arg Pro L eu Ser Gln Leu Pro Gly
                5                   10                  15

Lys Ala Leu Ser Val Cys Asp Arg Glu Asn G ly Thr Arg His Thr Leu
            20                  25                  30

Leu Phe Tyr Pro Ala Ser Phe Ser Pro Asp T hr Arg Arg Thr Tyr Thr
        35                  40                  45

Ser Gln Ala Asp Ala Ala Ser Gly Lys Ala V al Leu Val Thr Gly Cys
50                  55                  60

Asp Ser Gly Phe Gly Phe Ser Leu Ala Lys H is Leu His Ser Lys Gly
65                  70                  75                  80

Phe Leu Val Phe Ala Gly Cys Leu Leu Lys G lu Gln Gly Asp Ala Gly
                85                  90                  95

Val Arg Glu Leu Asp Ser Leu Lys Ser Asp A rg Leu Arg Thr Ile Gln
            100                 105                 110

Leu Asn Val Cys Asn Ser Glu Glu Val Glu L ys Ala Val Glu Thr Val
        115                 120                 125

Arg Ser Gly Leu Lys Asp Pro Glu Lys Gly M et Trp Gly Leu Val Asn
    130                 135                 140

Asn Ala Gly Ile Ser Thr Phe Gly Glu Val G lu Phe Thr Ser Met Glu
145                 150                 155                 160

Thr Tyr Lys Glu Val Ala Glu Val Asn Leu T rp Gly Thr Val Arg Thr
                165                 170                 175

Thr Lys Ser Phe Leu Pro Leu Leu Arg Arg A la Lys Gly Arg Val Val
            180                 185                 190

Asn Ile Ser Ser Met Leu Gly Arg Met Ala A sn Pro Ala Arg Ser Pro
        195                 200                 205

Tyr Cys Ile Thr Lys Phe Gly Val Glu Ala P he Ser Asp Cys Leu Arg
    210                 215                 220

Tyr Glu Met His Pro Leu Gly Val Lys Val S er Val Val Glu Pro Gly
```

```
225                 230                 235                 240

Asn Phe Ile Ala Ala Thr Ser Leu Tyr Ser Pro Glu Arg Ile Gln Ala
                245                 250                 255

Ile Ala Lys Lys Met Trp Asp Glu Leu Pro Glu Val Val Arg Lys Asp
                260                 265                 270

Tyr Gly Lys Lys Tyr Phe Asp Glu Lys Ile Ala Lys Met Glu Thr Tyr
                275                 280                 285

Cys Asn Ser Gly Ser Thr Asp Thr Ser Ser Val Ile Asn Ala Val Thr
                290                 295                 300

His Ala Leu Thr Ala Ala Thr Pro Tyr Thr Arg Tyr His Pro Met Asp
305                 310                 315                 320

Tyr Tyr Trp Trp Leu Arg Met Gln Val Met Thr His Phe Pro Gly Ala
                325                 330                 335

Ile Ser Asp Lys Ile Tyr Ile His
                340

(2) INFORMATION FOR SEQ ID NO: 12:

(i) SEQUENCE CHARACTERISTICS:
        (A) LENGTH:  327 amino acids
        (B) TYPE: amino acid
        (D) TOPOLOGY: linear (ii) MOLECULE TYPE: protein (ix) FEATURE:
        (A) NAME/KEY: Human estradiol 17-b dehydrogenase (hEDH)

(xi) SEQUENCE DESCRIPTION: SEQ ID NO:12:

Ala Arg Thr Val Val Leu Ile Thr Gly Cys Ser Ser Gly Ile Gly Leu
                5                  10                  15

His Leu Ala Val Arg Leu Ala Ser Asp Pro Ser Gln Ser Phe Lys Val
                20                  25                  30

Tyr Ala Thr Leu Arg Asp Leu Lys Thr Gln Gly Arg Leu Trp Glu Ala
                35                  40                  45

Ala Arg Ala Leu Ala Cys Pro Pro Gly Ser Leu Glu Thr Leu Gln Leu
    50                  55                  60

Asp Val Arg Asp Ser Lys Ser Val Ala Ala Ala Arg Glu Arg Val Thr
65                  70                  75                  80

Glu Gly Arg Val Asp Val Leu Val Cys Asn Ala Gly Leu Gly Leu Leu
                85                  90                  95

Gly Pro Leu Glu Ala Leu Gly Glu Asp Ala Val Ala Ser Val Leu Asp
                100                 105                 110

Val Asn Val Val Gly Thr Val Arg Met Leu Gln Ala Phe Leu Pro Asp
                115                 120                 125

Met Lys Arg Arg Gly Ser Gly Arg Val Leu Val Thr Gly Ser Val Gly
130                 135                 140

Gly Leu Met Gly Leu Pro Phe Asn Asp Val Tyr Cys Ala Ser Lys Phe
145                 150                 155                 160

Ala Leu Glu Gly Leu Cys Glu Ser Leu Ala Val Leu Leu Leu Pro Phe
                165                 170                 175

Gly Val His Leu Ser Leu Ile Glu Cys Gly Pro Val His Thr Ala Phe
                180                 185                 190

Met Glu Lys Val Leu Gly Ser Pro Glu Glu Val Leu Asp Arg Thr Asp
                195                 200                 205

Ile His Thr Phe His Arg Phe Tyr Gln Tyr Leu Ala His Ser Lys Gln
                210                 215                 220
```

Val Phe Arg Glu Ala Ala Gln Asn Pro Glu Glu Val Ala Glu Val Phe
225                 230                 235                 240

Leu Thr Ala Leu Arg Ala Pro Lys Pro Thr Leu Arg Tyr Phe Thr Thr
            245                 250                 255

Glu Arg Phe Leu Pro Leu Leu Arg Met Arg Leu Asp Asp Pro Ser Gly
            260                 265                 270

Ser Asn Tyr Val Thr Ala Met His Arg Glu Val Phe Gly Asp Val Pro
        275                 280                 285

Ala Lys Ala Glu Ala Gly Ala Glu Ala Gly Gly Ala Gly Pro Gly
    290                 295                 300

Ala Glu Asp Glu Ala Gly Arg Ser Ala Val Gly Asp Pro Glu Leu Gly
305                 310                 315                 320

Asp Pro Pro Ala Ala Pro Gln
            325

(2) INFORMATION FOR SEQ ID NO: 13:

(i) SEQUENCE CHARACTERISTICS:
        (A) LENGTH: 244 amino acids
        (B) TYPE: amino acid
        (D) TOPOLOGY: linear (ii) MOLECULE TYPE: protein (ix) FEATURE:
        (A) NAME/KEY:E.coli 3-oxo acyl[acyl carrier protein]reductase
        (FABG)

(xi) SEQUENCE DESCRIPTION: SEQ ID NO:13:

Met Asn Phe Glu Gly Lys Ile Ala Leu Val Thr Gly Ala Ser Arg Gly
            5                   10                  15

Ile Gly Arg Ala Ile Ala Glu Thr Leu Ala Ala Arg Gly Gly Lys Val
            20                  25                  30

Ile Gly Thr Ala Thr Ser Glu Asn Gly Ala Gln Ala Ile Ser Asp Tyr
        35                  40                  45

Leu Gly Ala Asn Gly Lys Gly Leu Met Leu Asn Val Thr Asp Pro Ala
    50                  55                  60

Ser Ile Glu Ser Val Leu Glu Lys Ile Arg Ala Glu Phe Gly Glu Val
65                  70                  75                  80

Asp Ile Leu Val Asn Asn Ala Gly Ile Thr Arg Asp Asn Leu Leu Met
            85                  90                  95

Arg Met Lys Asp Glu Glu Trp Asn Asp Ile Ile Glu Thr Asn Leu Ser
            100                 105                 110

Ser Val Phe Arg Leu Ser Lys Ala Val Met Arg Ala Met Met Lys Lys
        115                 120                 125

Arg His Gly Arg Ile Ile Thr Ile Gly Ser Val Val Gly Thr Met Gly
    130                 135                 140

Asn Gly Gly Gln Ala Asn Tyr Ala Ala Lys Ala Gly Leu Ile Gly
145                 150                 155                 160

Phe Ser Lys Ser Leu Ala Arg Glu Val Ala Ser Arg Gly Ile Thr Val
            165                 170                 175

Asn Val Val Ala Pro Gly Phe Ile Glu Thr Asp Met Thr Arg Ala Leu
            180                 185                 190

Ser Asp Asp Gln Arg Ala Gly Ile Leu Ala Gln Val Pro Ala Gly Arg
        195                 200                 205

Leu Gly Gly Ala Gln Glu Ile Ala Asn Ala Val Ala Phe Leu Ala Ser
    210                 215                 220

Asp Glu Ala Ala Tyr Ile Thr Gly Glu Thr Leu His Val Asn Gly Gly
225                 230                 235                 240

Met Tyr Met Val (2) INFORMATION FOR SEQ ID NO: 14:

(i) SEQUENCE CHARACTERISTICS:
        (A) LENGTH: 1128 base pairs
        (B) TYPE: nucleic acid
        (C) STRANDEDNESS: double
        (D) TOPOLOGY: linear (ii) MOLECULE TYPE: nucleic acid (ix) FEATURE:
        (A) NAME/KEY: human 11-cis retinol dehydrogenase (xi) SEQUENCE DESCRIPTION: SEQ ID NO: 14:

```
TAAGCTTCGG GCGCTGTAGT ACCTGCCAGC TTTCGCCACA GGAGGCTGCC A CCTGTAGGT      60
CACTTGGGCT CCAGCTATGT GGCTGCCTCT TCTGCTGGGT GCCTTACTCT G GGCAGTGCT     120
GTGGTTGCTC AGGGACCGGC AGAGCCTGCC CGCCAGCAAT GCCTTTGTCT T CATCACCGG     180
CTGTGACTCA GGCTTTGGGC GCCTTCTGGC ACTGCAGCTG GACCAGAGAG G CTTCCGAGT     240
CCTGGCCAGC TGCCTGACCC CCTCCGGGGC CGAGGACCTG CAGCGGGTGG C CTCCTCCCG     300
CCTCCACACC ACCCTGTTGG ATATCACTGA TCCCCAGAGC GTCCAGCAGG C AGCCAAGTG     360
GGTGGAGATG CACGTTAAGG AAGCAGGGCT TTTTGGTCTG GTGAATAATG C TGGTGTGGC     420
TGGTATCATC GGACCCACAC CATGGCTGAC CCGGGACGAT TTCCAGCGGG T GCTGAATGT     480
GAACACAATG GGTCCCATCG GGGTCACCCT TGCCCTGCTG CCTCTGCTGC A GCAAGCCCG     540
GGGCCGGGTG ATCAACATCA CCAGCGTCCT GGGTCGCCTG GCAGCCAATG G TGGGGGCTA     600
CTGTGTCTCC AAATTTGGCC TGGAGGCCTT CTCTGACAGC CTGAGGCGGG A TGTAGCTCA     660
TTTTGGGATA CGAGTCTCCA TCGTGGAGCC TGGCTTCTTC CGAACCCCTG T GACCAACCT     720
GGAGAGTCTG GAGAAAACCC TGCAGGCCTG CTGGGCACGG CTGCCTCCTG C CACACAGGC     780
CCACTATGGG GGGGCCTTCC TCACCAAGTA CCTGAAAATG CAACAGCGCA T CATGAACCT     840
GATCTGTGAC CCGGACCTAA CCAAGGTGAG CCGATGCCTG GAGCATGCCC T GACTGCTCG     900
ACACCCCCGA ACCCGCTACA GCCCAGGTTG GGATGCCAAG CTGCTCTGGC T GCCTGCCTC     960
CTACCTGCCA GCCAGCCTGG TGGATGCTGT GCTCACCTGG GTCCTTCCCA A GCCTGCCCA    1020
AGCAGTCTAC TGAATCCAGC CTTCCAGCAA GAGATTGTTT TTCAAGGACA A GGACTTTGA    1080
TTTATTTCTG CCCCCACCCT GGTACTGCCT GGTGCCTGCC ACAAAATA               1128
```

(2) INFORMATION FOR SEQ ID NO: 15:

(i) SEQUENCE CHARACTERISTICS:
        (A) LENGTH: 318 amino acids
        (B) TYPE: amino acid
        (D) TOPOLOGY: linear (ii) MOLECULE TYPE: protein (ix) FEATURE:
        (A) NAME/KEY: human 11-cis retinol dehydrogenase (xi) SEQUENCE DESCRIPTION: SEQ ID NO: 15:

Met Trp Leu Pro Leu Leu Leu Gly Ala Leu Leu Trp Ala Val Leu Trp
             5                  10              15

Leu Leu Arg Asp Arg Gln Ser Leu Pro Ala Ser Asn Ala Phe Val Phe

```
            20                  25                  30
Ile Thr Gly Cys Asp Ser Gly Phe Gly Arg Leu Leu Ala Leu Gln Leu
            35                  40                  45

Asp Gln Arg Gly Phe Arg Val Leu Ala Ser Cys Leu Thr Pro Ser Gly
            50                  55                  60

Ala Glu Asp Leu Gln Arg Val Ala Ser Ser Arg Leu His Thr Thr Leu
65                  70                  75                  80

Leu Asp Ile Thr Asp Pro Gln Ser Val Gln Gln Ala Ala Lys Trp Val
                85                  90                  95

Glu Met His Val Lys Glu Ala Gly Leu Phe Gly Leu Val Asn Asn Ala
                100                 105                 110

Gly Val Ala Gly Ile Ile Gly Pro Thr Pro Trp Leu Thr Arg Asp Asp
            115                 120                 125

Phe Gln Arg Val Leu Asn Val Asn Thr Met Gly Pro Ile Gly Val Thr
        130                 135                 140

Leu Ala Leu Leu Pro Leu Leu Gln Gln Ala Arg Gly Arg Val Ile Asn
145                 150                 155                 160

Ile Thr Ser Val Leu Gly Arg Leu Ala Ala Asn Gly Gly Gly Tyr Cys
                165                 170                 175

Val Ser Lys Phe Gly Leu Glu Ala Phe Ser Asp Ser Leu Arg Arg Asp
                180                 185                 190

Val Ala His Phe Gly Ile Arg Val Ser Ile Val Glu Pro Gly Phe Phe
            195                 200                 205

Arg Thr Pro Val Thr Asn Leu Glu Ser Leu Glu Lys Thr Leu Gln Ala
        210                 215                 220

Cys Trp Ala Arg Leu Pro Pro Ala Thr Gln Ala His Tyr Gly Gly Ala
225                 230                 235                 240

Phe Leu Thr Lys Tyr Leu Lys Met Gln Gln Arg Ile Met Asn Leu Ile
                245                 250                 255

Cys Asp Pro Asp Leu Thr Lys Val Ser Arg Cys Leu Glu His Ala Leu
            260                 265                 270

Thr Ala Arg His Pro Arg Thr Arg Tyr Ser Pro Gly Trp Asp Ala Lys
        275                 280                 285

Leu Leu Trp Leu Pro Ala Ser Tyr Leu Pro Ala Ser Leu Val Asp Ala
        290                 295                 300

Val Leu Thr Trp Val Leu Pro Lys Pro Ala Gln Ala Val Tyr
305                 310                 315

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: nucleic acid (ix) FEATURE:
        (A) NAME/KEY: PCR primer (xi) SEQUENCE DESCRIPTION: SEQ ID NO:16:

ACGTGAATTC TGYGAYTCNG GNWTYGG                                    27

(2) INFORMATION FOR SEQ ID NO:17:

(i) SEQUENCE CHARACTERISTICS:
        (A) LENGTH: 25 base pairs
```

```
        (B) TYPE: nucleic acid
        (C) STRANDEDNESS: single
        (D) TOPOLOGY: linear (ii) MOLECULE TYPE: nucleic acid (ix) FEATURE:
        (A) NAME/KEY: PCR primer (xi) SEQUENCE DESCRIPTION: SEQ ID NO:17:

ACGTGAATTC TTNGCRTCCC CANCC                                              25

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: nucleic acid (ix) FEATURE:
        (A) NAME/KEY: PCR primer (xi) SEQUENCE DESCRIPTION: SEQ ID NO:18:

ACGTGAATTC GARGCNTTYT CNGA                                               24

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: nucleic acid (ix) FEATURE:
        (A) NAME/KEY: PCR primer (xi) SEQUENCE DESCRIPTION: SEQ ID NO:19:

ACGTGAATTC CGNGTNCKNG GRTG                                               24

(2) INFORMATION FOR SEQ ID NO: 20:

(i) SEQUENCE CHARACTERISTICS:
        (A) LENGTH: 262 base pairs
        (B) TYPE: nucleic acid
        (C) STRANDEDNESS: double
        (D) TOPOLOGY: linear (ii) MOLECULE TYPE: nucleic acid (ix) FEATURE:
        (A) NAME/KEY: PCR clone 194

(xi) SEQUENCE DESCRIPTION: SEQ ID NO: 20:

CTCTCTCAGA AGGGAGCTCT CCTACTTCGG AGTGAAGGTG GCTATGATTG AGCCTGGTTA         60

CTTTGTTACC AATATGACCC AAGATGAGGG TTTTATTGGA TACCTCCAGG CATTGTGGAA        120

CCGGGCCAGC CCAGAGCTGA AGAACTCTA TGGAGAAAAC TTCCCTGCTG ACTTCTTGAA         180

GACATTGAGT TTACTGAAAC CACGGTGGAC TCAGAATCTG TCCTTGGTGA CCGACTGCAT        240

GGAGCACGCC CTGACTGCCT GC                                                262

(2) INFORMATION FOR SEQ ID NO:21:

(i) SEQUENCE CHARACTERISTICS:
```

(A) LENGTH: 262 base pairs
            (B) TYPE: nucleic acid
            (C) STRANDEDNESS: double
            (D) TOPOLOGY: linear (ii) MOLECULE TYPE: nucleic acid (ix) FEATURE:
            (A) NAME/KEY: PCR clone 207

(xi) SEQUENCE DESCRIPTION: SEQ ID NO:21:

CTCCCTCAGG AGGGGGCTCT CCTACTTTGG GGTGAAGGTG GCTATTATAG A GCCTGGCTT    60

CTTCCTGACC GGTGTGACCA GTAGTGCCAG ATTATGCTCA AATACCCAGA T GCTGTGGGA   120

CCAGACCAGC TCAGAAATCA GGGAGATCTA TGGCGAGAAG TACCTGGCAT C CTATCTGAA   180

AAGGCTAAAC GAATTGGACA AGAGGTGCAA CAAGGACCTG TCTTTGGTGA C TGACTGCAT   240

GGAGCATGCT CTGACTGCCT GC                                            262

(2) INFORMATION FOR SEQ ID NO:22:

(i) SEQUENCE CHARACTERISTICS:
            (A) LENGTH: 265 base pairs
            (B) TYPE: nucleic acid
            (C) STRANDEDNESS: double
            (D) TOPOLOGY: linear (ii) MOLECULE TYPE: nucleic acid (ix) FEATURE:
            (A) NAME/KEY: PCR clone 200

(xi) SEQUENCE DESCRIPTION: SEQ ID NO:22:

CAGCCTGAGG CGGGACATGG CTCCGTTCGG AGTACAAGTC TCCATTGTGG AGCCTGGCTT    60

CTTTCGAACC CCTGTGACCA ACCTGGAGAG TCTGGAGAGC ACCCTGAAGG C TTGTTGGGC   120

CCGGCTACCT CCAGCTATAC AGGCCCACTA CGGGGAGGCC TTCCTCGATA C TCATCTTCG   180

AGTACAGCGC CGCATCATGA ACCTGATCTG TGACCCAGAA CTAACGAAGG T GACCAGCTG   240

CCTGGAGCAT GCCCTGACTG CTCGC                                    265

(2) INFORMATION FOR SEQ ID NO:23:

(i) SEQUENCE CHARACTERISTICS:
            (A) LENGTH: 265 base pairs
            (B) TYPE: nucleic acid
            (C) STRANDEDNESS: double
            (D) TOPOLOGY: linear (ii) MOLECULE TYPE: nucleic acid (ix) FEATURE:
            (A) NAME/KEY: PCR clone 215

(xi) SEQUENCE DESCRIPTION: SEQ ID NO:23:

CAGCCTGAGG CGAGATGTGG CTCCTTTTGG GGTACGGGTC TCTATCGTGG A ACCTGGCTT    60

CTTCCGAACC CCTGTGACAA ACCTGGAAAC TTTGGAGGGC ACCCTGCAGG C CTGCTGGGC   120

ACGGCTGCCT CCAGCCACAC AGGCCCTCTA TGGGGAGGCC TTCCTCACCA A ATACCTGAG   180

AGTGCAGCAA CGTATCATGA ACATGATCTG TGATCCGGAC CTGGCCAAGG T GAGCAGGTG   240

CCTGGAGCAT GCCCTAACTG CCCGT                                         265

(2) INFORMATION FOR SEQ ID NO:24:

(i) SEQUENCE CHARACTERISTICS:
            (A) LENGTH: 87 amino acids (B) TYPE: amino acid
(D) TOPOLOGY: linear (ii) MOLECULE TYPE: protein (ix) FEATURE:
(A) NAME/KEY: PCR clone 194

(xi) SEQUENCE DESCRIPTION: SEQ ID NO:24 :

Ser Leu Arg Arg Glu Leu Ser Tyr Phe Gly Val Lys Val Ala Met Ile
                 5                  10                 15

Glu Pro Gly Tyr Phe Val Thr Asn Met Thr Gln Asp Glu Gly Phe Ile
             20                 25                 30

Gly Tyr Leu Gln Ala Leu Trp Asn Arg Ala Ser Pro Glu Leu Lys Glu
         35                 40                 45

Leu Tyr Gly Glu Asn Phe Pro Ala Asp Phe Leu Lys Thr Leu Ser Leu
 50                 55                 60

Leu Lys Pro Arg Trp Thr Gln Asn Leu Ser Leu Val Thr Asp Cys Met
 65                 70                 75                 80

Glu His Ala Leu Thr Ala Cys
             85

(2) INFORMATION FOR SEQ ID NO:25:

(i) SEQUENCE CHARACTERISTICS:
        (A) LENGTH:87 amino acids
        (B) TYPE: amino acid
        (D) TOPOLOGY: linear (ii) MOLECULE TYPE: protein (ix) FEATURE:
        (A) NAME/KEY: PCR clone 207

(xi) SEQUENCE DESCRIPTION: SEQ ID NO:25:

Ser Leu Arg Arg Gly Leu Ser Tyr Phe Gly Val Lys Val Ala Ile Ile
                 5                  10                 15

Glu Pro Gly Phe Phe Leu Thr Gly Val Thr Ser Ser Ala Arg Leu Cys
             20                 25                 30

Ser Asn Thr Gln Met Leu Trp Asp Gln Thr Ser Ser Glu Ile Arg Glu
         35                 40                 45

Ile Tyr Gly Glu Lys Tyr Leu Ala Ser Tyr Leu Lys Arg Leu Asn Glu
 50                 55                 60

Leu Asp Lys Arg Cys Asn Lys Asp Leu Ser Leu Val Thr Asp Cys Met
 65                 70                 75                 80

Glu His Ala Leu Thr Ala Cys
             85

(2) INFORMATION FOR SEQ ID NO:26:

(i) SEQUENCE CHARACTERISTICS:
        (A) LENGTH: 88 amino acids
        (B) TYPE: amino acid
        (D) TOPOLOGY: linear (ii) MOLECULE TYPE: protein (ix) FEATURE:
        (A) NAME/KEY: PCR clone 200

(xi) SEQUENCE DESCRIPTION: SEQ ID NO: 26:

Ser Leu Arg Arg Asp Met Ala Pro Phe Gly Val Gln Val Ser Ile Val
                 5                  10                 15

```
Glu Pro Gly Phe Phe Arg Thr Pro Val Thr A sn Leu Glu Ser Leu Glu
        20                  25              30

Ser Thr Leu Lys Ala Cys Trp Ala Arg Leu P ro Pro Ala Ile Gln Ala
        35                  40              45

His Tyr Gly Glu Ala Phe Leu Asp Thr His L eu Arg Val Gln Arg Arg
 50                  55                  60

Ile Met Asn Leu Ile Cys Asp Pro Glu Leu T hr Lys Val Thr Ser Cys
65                  70                  75              80

Leu Glu His Ala Leu Thr Ala Arg
                85
```

(2) INFORMATION FOR SEQ ID NO:27:

(i) SEQUENCE CHARACTERISTICS:
        (A) LENGTH: 88 amino acids
        (B) TYPE: amino acid
        (D) TOPOLOGY: linear (ii) MOLECULE TYPE: protein (ix) FEATURE:
        (A) NAME/KEY: PCR clone 215

(xi) SEQUENCE DESCRIPTION: SEQ ID NO:27:

```
Ser Leu Arg Arg Asp Val Ala Pro Phe Gly V al Arg Val Ser Ile Val
                5                  10              15

Glu Pro Gly Phe Phe Arg Thr Pro Val Thr A sn Leu Glu Thr Leu Glu
        20                  25              30

Gly Thr Leu Gln Ala Cys Trp Ala Arg Leu P ro Pro Ala Thr Gln Ala
        35                  40              45

Leu Tyr Gly Glu Ala Phe Leu Thr Lys Tyr L eu Arg Val Gln Gln Arg
 50                  55                  60

Ile Met Asn Met Ile Cys Asp Pro Asp Leu A la Lys Val Ser Arg Cys
65                  70                  75              80

Leu Glu His Ala Leu Thr Ala Arg
                85
```

(2) INFORMATION FOR SEQ ID NO:28:

(i) SEQUENCE CHARACTERISTICS:
        (A) LENGTH: 563 base pairs
        (B) TYPE: nucleic acid
        (C) STRANDEDNESS: dou ble
        (D) TOPOLOGY: linear (ii) MOLECULE TYPE: nucleic acid (ix) FEATURE:
        (A) NAME/KEY: clone ME 207.

(xi) SEQUENCE DESCRIPTION: SEQ ID NO:28:

```
GAGGCGTTCT CGGACTCCCT CAGGAGGGGG CTCTCCTACT TTGGGGTGAA G GTGGCTATT      60

ATAGAGCCTG GCTTCTTCCT GACCGGTGTG ACCAGTAGTG CCAGATTATG C TCAAATACC    120

CAGATGCTGT GGGACCAGAC CAGCTCAGAA ATCAGGGAGA TCTATGGCGA G AAGTACCTG    180

GCATCCTATC TGAAAAGGCT AAACGAATTG GACAAGAGGT GCAACAAGGA C CTGTCTTTG    240

GTGACTGACT GCATGGAGCA TGCTCTGACT GCCTGCCACC CTCGCACGCG A TACTCAGCT    300

GGCTGGGATG CTAAGCTCTT CTACCTCCCC TTGAGCTACC TGCCTACCTT T CTTGTGGAT    360

GCCCTTCTCT ATTGGACTTC CCTGAAGCCT GAGAAAGCCC TCTGACGTGT T CACCTATGT    420

GCATACCTGG GGAGATGTAG GTAGAGTTTG AGAGAGAGAA TATTTAGGGA A ATTTGGAG     480
```

```
GGTTGAGGGA GGGAGTTTAT TACTCTGGGG TTCAGTCAAC ACACTTCATC T CATTAATTC      540

TCCTATGACA CTACTGAATA CTG                                              563
```

(2) INFORMATION FOR SEQ ID NO:29:

(i) SEQUENCE CHARACTERISTICS:
        (A) LENGTH: 134 amino acids
        (B) TYPE: amino acid
        (D) TOPOLOGY: linear (ii) MOLECULE TYPE: protein (ix) FEATURE:
        (A) NAME/KEY: clone ME 207

(xi) SEQUENCE DESCRIPTION: SEQ ID NO:29:

```
Glu Ala Phe Ser Asp Ser Leu Arg Arg Gly L eu Ser Tyr Phe Gly Val
            5                   10              15
Lys Val Ala Ile Ile Glu Pro Gly Phe Phe L eu Thr Gly Val Thr Ser
        20              25              30
Ser Ala Arg Leu Cys Ser Asn Thr Gln Met L eu Trp Asp Gln Thr Ser
    35              40              45
Ser Glu Ile Arg Glu Ile Tyr Gly Glu Lys T yr Leu Ala Ser Tyr Leu
    50              55              60
Lys Arg Leu Asn Glu Leu Asp Lys Arg Cys A sn Lys Asp Leu Ser Leu
65              70              75              80
Val Thr Asp Cys Met Glu His Ala Leu Thr A la Cys His Pro Arg Thr
                85              90              95
Arg Tyr Ser Ala Gly Trp Asp Ala Lys Leu P he Tyr Leu Pro Leu Ser
            100             105             110
Tyr Leu Pro Thr Phe Leu Val Asp Ala Leu L eu Tyr Trp Thr Ser Leu
        115             120             125
Lys Pro Glu Lys Ala Leu
    130
```

(2) INFORMATION FOR SEQ ID NO: 30:

(i) SEQUENCE CHARACTERISTICS:
        (A) LENGTH: 18 base pairs
        (B) TYPE: nucleic acid
        (C) STRANDEDNESS: sin gle
        (D) TOPOLOGY: linear (ii) MOLECULE TYPE: nucleic acid (ix) FEATURE:
        (A) NAME/KEY: forward primer (xi) SEQUENCE DESCRIPTION: SEQ ID NO:30:

```
GCTTCGGGCG CTGTAGTA                                                    18
```

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: sin gle
        (D) TOPOLOGY: linear (ii) MOLECULE TYPE: nucleic acid (ix) FEATURE:
        (A) NAME/KEY: Reverse primer (xi) SEQUENCE DESCRIPTION: SEQ ID NO:31:

AAAACAATCT CTTGCTGGAA                                             20

(2) INFORMATION FOR SEQ ID NO:32:

(i) SEQUENCE CHARACTERISTICS:
        (A) LENGTH: 1613 base pairs
        (B) TYPE: nucleic acid
        (C) STRANDEDNESS: dou ble
        (D) TOPOLOGY: linear (xi) SEQUENCE DESCRIPTION: SEQ ID NO:32:

```
CATCCATACT GGTCAGAGGA ACATGATAGA AACCTGACAT TCTCAGTGCC T ATACCTTCC    60
TGTGTAAGCA GCGGCCAGGC TCATTTTGAC ACAGAATATC TCTCTCTGCT T GACTTCTAC   120
AAACCATGTG GCTCTACCTG GTTGCACTGG TGGGCCTGTG GACGCTCCTG C GCTTCTTCA   180
GGGAGAGGCA GGTNGTGAGC CATCTCCAAG ACAAGTATGT CTTCATCACG G GCTGTGACT   240
CTGGCTTTGG GAACCTTCTG GCCAGACAAC TGGACAGGAG AGGCATGAGG G TGCTAGCTG   300
CATGTCTGAC GGAGAAGGGA GCTGAGCAGC TGAGGAACAA GACATCTGAC A GGCTGGAGA   360
CAGTGATCCT GGATGTCACC AAGACAGAGA GTATTGTGGC AGCCACTCAG T GGGTGAAGG   420
AGCGTGTTGG GAACAGAGGA CTCTGGGGCC TGGTCAACAA TGCTGGCATC T GTGTCTTTG   480
CTATCAATGA GTGGCTGAAA AAGAGGACT TTGCAAATAT ACTGGATGTG A ACCTGTTGG   540
GCATGATCGA GGTGACTCTG AGCATGCTGC CCTTAGTGAG GAAGGCGAGG G GCCGTGTGT   600
TCAACATCTC CAGCTCCATG GGTCGAGTGT CTTTGTGTGG TGGTGGTTAC T GCATCTCCA   660
AGTATGGTGT AGAGGCCTTC TCAGACTCCC TCAGGAGGGA GATCTCCTAT T TTGGGGTGA   720
AGGTGGCTAT CATAGAGCCT GGCGGGTTCA GGACTAATGT CTCCAACTAC G AGAGGCTAT   780
CACACAGCAT AGAGAAGCTG TGGGACCAGA CATCCTCGGA GGTCAAGGAG G TCTATGACA   840
AGAATTTTCT GGACTCCTAT ATCAAAGCAA TACAGTCATT GACAGACACA T GCTCAGATG   900
ACCTGTCTGT GGTAACTGAC TGCATGGAGC ACGTCTGAC TGCCTGTCAC C CTCGCACAA   960
GATACTCAGC TGGCTGGGAT GCCAAGCTCT TCTACCTACC CTTGAGCTAC A TGCCCACCT  1020
TCCTGGTAGA TGCCATGTTG TACTGGAGCT CTGTAAAGCC TGCCCAAGCC C TGTGAATCT  1080
GCACGTGTGT GCAGACTTGT GGCGGGTGGA GGGAGATAAT GGCACAGGGC A TGTGGTTCT  1140
TGAGACTCAT TAAAACAATT CAGCTTCCAT ACTACTCAGA ACCAGTAAAG T TCAGGGGAA  1200
AGAGGCAGTA AAGTTCTGCC AAGGGGGAGT GATACAAAGG GGCTGGCAAT A TCCTGTGAA  1260
CTTAGCTTCT TGGGGCTTCA TCTTGGCCTA TTGTGAGAAT CCACAGGACT G CAGAGATTG  1320
TAAACACCTA GGATGAGCTT TGCCTCTNNC CTTCCTCATG ATGTCCATGG G CCTGGCCAT  1380
CATGGAAGAT CGAAAGAATC CACTTCACAA TCACCTTTTT CCATGGTGTC A GGAGGGAGG  1440
GCCCCCACCC GCACTCCACA TCCTAATCGG CTTTAGGAGG TGGTTTTGCT G GTGGGATAG  1500
AATCTTGCTA AGATAAACAA CAACAACAAT TTTTATTTGT CTCAAAACCA T GGTTTTTCT  1560
TTGGATTCCT TTCATTTCAG AATAAAAGTT GAAAAGATAA AAAAAAAAA A AA        1613
```

(2) INFORMATION FOR SEQ ID NO:33:

(i) SEQUENCE CHARACTERISTICS:
        (A) LENGTH: 1384 base pairs
        (B) TYPE: nucleic acid
        (C) STRANDEDNESS: dou ble
        (D) TOPOLOGY: linear (xi) SEQUENCE DESCRIPTION: SEQ ID NO:33:

```
CTTTTTTTTT TTTTTTTTTG ACACAGAGTA TCTCTCTCTC TGCTTGACTT C TACAAGCCA    60
TGTGGCTCTA CCTGGTGGCA CTGGTGGGCC TGTGGACGCT TCTGCGCTTC T TCAGGGTGA   120
GGCAGGTGGT GAGCCATCTC CAAGACAAAT ATGTCTTCAT CACGGGCTGT G ACTCTGGCT   180
TTGGGACCCT GCTGGCCAGA CAGCTGGACA GGAGAGGCAT GAGGGTGCTG G CTGCATGTC   240
TGACGGAGAA GGGAGCCGAG GAGCTGAGGA ACAAGACATC TGACAGGCTG G AGACAGTGA   300
TCCTGGATGT CACCAAGACA GAGAGTATTG TGACAGCCAC TCAGTGGGTG A AGGAGCATG   360
TTGGGAACAG AGGACTCTGG GGCCTGGTCA ACAACGCTGG CATCTCCACC C CCTCGGGTC   420
CCAACGAGTG GATGAAAAAG CAGGACTTTG CACATGTACT GGATGTGAAC C TGTTGGGCA   480
TGATCGAGGT GACTCTGAGC ATGCTGCCTT TAGTGAGGAA GGCGAGGGGT C GTGTGGTCA   540
ACGTCTCCAG TGTCATGGGT CGAGTGTCTC TCTTTGGTGG TGGTTACTGC A TCTCTAAGT   600
ATGGTGTAGA GGCCTTCTCA GACTCCCTCA GGAGGGAGCC CCGCTACTTT G GGGTGAAGG   660
TGGCTATTAT AGAGCCTGGC TTCTTCCTGA CCGGTGTGAC CAGTAGTGCC A GATTATGCT   720
CAAATACCCA GATGCTGTGG GACCAGACCA GCTCAGAAAT CAGGGAGATC T ATGGCGAGA   780
AGTACCTGGC ATCCTATCTG AAAAGGCTAA ACAAATTGGA CAAGAGGTGC A ACAAGGACC   840
TGTCTGGGGT GACTGACTGC ATGGAGCATG CTCTGACTGC CTGTCACCCT C GTACCCGAT   900
ACTCAGCTGG CTGGGATGCT AAGCTCTTCT ACCTCCCCTT GAGCTACCTG C CCACCTTTC   960
TTGTGGATGC CCTTCTCTAC TGGACTTCCC TGAGGCCTGA AAAAGCCCTC T GAAAGTATT  1020
CACCTATGTG CATACCTGGG GAGATGTAGG TAGAGTTTGA GAGAGAGAAT A TTTAGGGGA  1080
AATTAGGAGA GTTGGGGGGG GATTTTATTA CTCTGGGGTT CAGTCAATAC A CTTCATCTT  1140
GTTAATTCTC CTATGACACT ACTCAAGACT GATGATGACC AAAGAAATAG G CAAAGAATT  1200
CTGCCAAGGG ATTCAGTTAC AAAAGAGCTG GCTGATGCCC AGATTATGAG C ATCATGGCT  1260
ACCATGAAGG TCCACACAGA TGAGGAGGCT GGGACAAGTT TGTGCCAAAG C ACTCTCCTG  1320
TGGTCCTCCT CTGCAGGAAA TGTACATGCC CTGGCTAGTT TAAACCCCTA T GCAAGATGG  1380
AATT                                                                1384
```

(2) INFORMATION FOR SEQ ID NO:34:

(i) SEQUENCE CHARACTERISTICS:
        (A) LENGTH: 1240 base pairs
        (B) TYPE: nucleic acid
        (C) STRANDEDNESS: dou ble
        (D) TOPOLOGY: linear (xi) SEQUENCE DESCRIPTION: SEQ ID NO:34:

```
CTTCTCTCTC TCTCTCTCTC TCTCTCCTCT TCTACAAACC ATGTGGCTCT A CATGGTGGC    60
GCTACTGGGC CTGTGGATGC TCCTGCGCTT TTTTAGAGAG AGGCAAGTGG T GGACCATCT   120
TCAAGACAAG TATGTCTTCA TCACAGGCTG TGGCTCTGGC TTTGGGAACC T GCTGGCCAG   180
ACAGCTGGAC AGGAGAGGCA TGAGAGTGTT GGCTGCATGT CGGAAGGAGG A GGGAGCCGA   240
GGAGCTGAGG AGAAAGACAT CAGAAAGGCT GGAGACAGTG ATCCTGGATG T CACCAAGAC   300
AGAGAATATT GTGGCAGCCA CTCAGTGGGT GAAGGAGCGT GTTGGGAACA G AGGACTCTG   360
GGGCCTGGTC AACAACGCTG GCATCTCCGT CCCCTCGGGT CCCAACGAGT G GATGAAAAA   420
ACAGGACTTT GCAAGTGTAC TGGATGTGAA CCTGTTGGGC TTGATCGAGG T GACTCTGAG   480
CATGCTGCCC TTAGTGAGGA AGGCGAGGGG CCGTGTGGTC AACGTCTCCA G CATCTTGGG   540
CAGAGTGTCA CTTGGTGGTA GTGGTGGTTA CTGCATCTCC AAGTATGGTA T AGAGGCCTT   600
```

```
CTCAGACTCC CTTAGGAGGG ACGTCCGCTA CTTTGGGGTG AAGGTGGCTA T TATAGAGCC    660

TGGCTTCTTC CTGACTGGTA TGGCCAGTAG TGCCAGATTA TGCTCAAATA T CCAGATGCT    720

GTGGGACCAG ACCAGCTCAG AAATGCGGGA GATCTATGGA GAGAAATACC T GGCATCCTA    780

TCTGAAAAAC CTAAACGAAT TGGACCAGAG GTGCAACAAG GACCTGTCTG T GGTGACTGA    840

CTGCATGGAG CACGCTCTGA CTGCCTGTCA CCCTCGCACG AGATACTCAG C TGGCTGGGA    900

TGCTAAGCTC TTCTTCACCC CCTTGAGCTA CCTGCCCACC TTTCTTGTGG A TGCTCTTCT    960

ATACTGGACT TCTCCAAAAC CTGACAAAGC CCTGTGAAAG CTAGATCCTT T TGTGTTGTT   1020

GGGTCAATGG AAGTGCTGTG TGAGGGTGCA GANNCTCAGG AGGAGGAAGA T TCCTGTTCT   1080

CAGCCCACAT GTGCTGTGCA TAGGTGCCTG GCTTTTTCTT CCTCTGTATA A CATGGGGGA   1140

CATGGGACCA CAGGAATCTG CTATGCTTAA ATGATCATTA CCATTGTTGG T GAAAGAAAA   1200

AAAACGACCT CCCCTGTCTC GGGTTAAAAA AAAAAAAAA                            1240
```

(2) INFORMATION FOR SEQ ID NO:35:

(i) SEQUENCE CHARACTERISTICS:
        (A) LENGTH: 1146 base pairs
        (B) TYPE: nucleic acid
        (C) STRANDEDNESS: dou ble
        (D) TOPOLOGY: linear (xi) SEQUENCE DESCRIPTION: SEQ ID NO:35:

```
CGCTTGAGAG CTTTCCCCAG AGGCTGCCCT CAGCAGGGCA TCTCATCCCA T CATGTGGCT     60

GCCTCTGCTT CTGGGTGCCT TGCTGTGGGC AGTGCTGTGG TTGCTCAGAG A CCGGCAGAG    120

CCTGCCGGCC AGTGATGCTT TCATCTTCAT CACTGGCTGT GACTCTGGCT T TGGGCGCCT    180

CCTGGCACTG CAACTTGACC AGAAGGGCTT CCAAGTCCTG GCCGGCTGCC T GACCCCCTC    240

TGGAGCAGAA GACCTGCAGC AGATGGCCTC CTCCCGCCTC CACACAACAC T ACTGGATAT    300

CACTGATCCC CAGAATGTCC AGCAAGTTGC CAAGTGGGTG AAGACACGTG T TGGAGAAAC    360

TGGACTTTTT GGTCTGGTGA ATAACGCTGG CGTAGCTGGT ATCATCGGGC C CACACCATG    420

GCTAACACAG GATGATTTCC AGAGAGTACT GAGTGTGAAC ACACTGGGGC C CATCGGTGT    480

CACCCTTGCC CTGCTGCCCC TGCTACAGCA GGCCAGGGGT CGGGTGGTCA A CATCACCAG    540

TGTCTTGGGC CGCATAGCAG CCAATGGCGG GGGCTACTGT GTCTCCAAGT T TGGCCTGGA    600

GGCCTTCTCT GACAGCCTGA GGCGGGACAT GGCTCCGTTC GGAGTACAAG T CTCCATTGT    660

GGAGCCTGGC TTCTTTCGAA CCCCTGTGAC CAACCTGGAG AGTCTGGAGA G CACCCTGAA    720

GGCTTGTTGG GCCCGGCTAC CTCCAGCTAT ACAGGCCCAC TACGGGGAAG C CTTCCTCGA    780

TACTTATCTT CGAGTACAGC GCCGCATCAT GAACCTGATC TGTGACCCAG A ACTAACGAA    840

GGTGACCAGC TGCCTGGAGC ATGCCCTGAC TGCTCGCCAC CCCCGAACAC G CTACAGCCC    900

AGGCTGGGAT GCCAAGCTGC TCTGGCTGCC TGCCTCCTAC CTTCCAGCCA G GGTGGTGGA    960

TGCTGTGCTC ACCTGGATCC TTCCCCGGCC CGCCCAGTCA GTCTCCTGAT T CCAGCTTTA   1020

CAGCAAGAGG CTGATTTTGA AAAGCAAGGC ATCTATTTCT GTGTCTACCC A GTGCTGCCT   1080

GGTTTCTGAT ACCAATTAGG CTCTCAATAA ATATGTATTG CTTTAAAAAA A AAAAAAAA   1140

AAAAAG                                                                1146
```

(2) INFORMATION FOR SEQ ID NO:36:

(i) SEQUENCE CHARACTERISTICS:
        (A) LENGTH: 316 amino acids (B) TYPE: amino acid
        (D) TOPOLOGY: linear (xi) SEQUENCE DESCRIPTION: SEQ ID NO:36:

Met Trp Leu Tyr Leu Val Ala Leu Val Gly Leu Trp Thr Leu Leu Arg
                 5                  10                  15

Phe Phe Arg Glu Arg Gln Val Val Ser His Leu Gln Asp Lys Tyr Val
             20                  25                  30

Phe Ile Thr Gly Cys Asp Ser Gly Phe Gly Asn Leu Leu Ala Arg Gln
         35                  40                  45

Leu Asp Arg Arg Gly Met Arg Val Leu Ala Ala Cys Leu Thr Glu Lys
 50                  55                  60

Gly Ala Glu Gln Leu Arg Asn Lys Thr Ser Asp Arg Leu Glu Thr Val
 65                  70                  75                  80

Ile Leu Asp Val Thr Lys Thr Glu Ser Ile Val Ala Ala Thr Gln Trp
                 85                  90                  95

Val Lys Glu Arg Val Gly Asn Arg Gly Leu Trp Gly Leu Val Asn Asn
            100                 105                 110

Ala Gly Ile Cys Val Phe Ala Ile Asn Glu Trp Leu Lys Lys Glu Asp
        115                 120                 125

Phe Ala Asn Ile Leu Asp Val Asn Leu Leu Gly Met Ile Glu Val Thr
130                 135                 140

Leu Ser Met Leu Pro Leu Val Arg Lys Ala Arg Gly Arg Val Phe Asn
145                 150                 155                 160

Ile Ser Ser Ser Met Gly Arg Val Ser Leu Cys Gly Gly Gly Tyr Cys
                165                 170                 175

Ile Ser Lys Tyr Gly Val Glu Ala Phe Ser Asp Ser Leu Arg Arg Glu
            180                 185                 190

Ile Ser Tyr Phe Gly Val Lys Val Ala Ile Ile Glu Pro Gly Gly Phe
        195                 200                 205

Arg Thr Asn Val Ser Asn Tyr Glu Arg Leu Ser His Ser Ile Glu Lys
210                 215                 220

Leu Trp Asp Gln Thr Ser Ser Glu Val Lys Glu Val Tyr Asp Lys Asn
225                 230                 235                 240

Phe Leu Asp Ser Tyr Ile Lys Ala Ile Gln Ser Leu Thr Asp Thr Cys
                245                 250                 255

Ser Asp Asp Leu Ser Val Val Thr Asp Cys Met Glu His Ala Leu Thr
            260                 265                 270

Ala Cys His Pro Arg Thr Arg Tyr Ser Ala Gly Trp Asp Ala Lys Leu
        275                 280                 285

Phe Tyr Leu Pro Leu Ser Tyr Met Pro Thr Phe Leu Val Asp Ala Met
290                 295                 300

Leu Tyr Trp Ser Ser Val Lys Pro Ala Gln Ala Leu
305                 310                 315

(2) INFORMATION FOR SEQ ID NO:37:

(i) SEQUENCE CHARACTERISTICS:
        (A) LENGTH: 317 amino acids
        (B) TYPE: amino acid
        (D) TOPOLOGY: linear (xi) SEQUENCE DESCRIPTION: SEQ ID NO:37:

Met Trp Leu Tyr Leu Val Ala Leu Val Gly Leu Trp Thr Leu Leu Arg
                 5                  10                  15

Phe Phe Arg Val Arg Gln Val Val Ser His Leu Gln Asp Lys Tyr Val

-continued

```
                    20                  25                  30
Phe Ile Thr Gly Cys Asp Ser Gly Phe Gly Thr Leu Leu Ala Arg Gln
                35                  40                  45
Leu Asp Arg Arg Gly Met Arg Val Leu Ala Ala Cys Leu Thr Glu Lys
     50                  55                  60
Gly Ala Glu Glu Leu Arg Asn Lys Thr Ser Asp Arg Leu Glu Thr Val
 65                  70                  75                  80
Ile Leu Asp Val Thr Lys Thr Glu Ser Ile Val Thr Ala Thr Gln Trp
                85                  90                  95
Val Lys Glu His Val Gly Asn Arg Gly Leu Trp Gly Leu Val Asn Asn
                100                 105                 110
Ala Gly Ile Ser Thr Pro Ser Gly Pro Asn Glu Trp Met Lys Lys Gln
                115                 120                 125
Asp Phe Ala His Val Leu Asp Val Asn Leu Leu Gly Met Ile Glu Val
            130                 135                 140
Thr Leu Ser Met Leu Pro Leu Val Arg Lys Ala Arg Gly Arg Val Val
145                 150                 155                 160
Asn Val Ser Ser Val Met Gly Arg Val Ser Leu Phe Gly Gly Gly Tyr
                165                 170                 175
Cys Ile Ser Lys Tyr Gly Val Glu Ala Phe Ser Asp Ser Leu Arg Arg
                180                 185                 190
Glu Leu Arg Tyr Phe Gly Val Lys Val Ala Ile Ile Glu Pro Gly Phe
            195                 200                 205
Phe Leu Thr Gly Val Thr Ser Ser Ala Arg Leu Cys Ser Asn Thr Gln
            210                 215                 220
Met Leu Trp Asp Gln Thr Ser Ser Glu Ile Arg Glu Ile Tyr Gly Glu
225                 230                 235                 240
Lys Tyr Leu Ala Ser Tyr Leu Lys Arg Leu Asn Lys Leu Asp Lys Arg
                245                 250                 255
Cys Asn Lys Asp Leu Ser Gly Val Thr Asp Cys Met Glu His Ala Leu
            260                 265                 270
Thr Ala Cys His Pro Arg Thr Arg Tyr Ser Ala Gly Trp Asp Ala Lys
            275                 280                 285
Leu Phe Tyr Leu Pro Leu Ser Tyr Leu Pro Thr Phe Leu Val Asp Ala
            290                 295                 300
Leu Leu Tyr Trp Thr Ser Leu Arg Pro Glu Lys Ala Leu
305                 310                 315

(2) INFORMATION FOR SEQ ID NO:38:

(i) SEQUENCE CHARACTERISTICS:
        (A) LENGTH: 318 amino acids
        (B) TYPE: amino acid
        (D) TOPOLOGY: linear (xi) SEQUENCE DESCRIPTION: SEQ ID NO:38:

Met Trp Leu Tyr Met Val Ala Leu Leu Gly Leu Trp Met Leu Leu Arg
                 5                  10                  15
Phe Phe Arg Glu Arg Gln Val Val Asp His Leu Gln Asp Lys Tyr Val
                20                  25                  30
Phe Ile Thr Gly Cys Gly Ser Gly Phe Gly Asn Leu Leu Ala Arg Gln
                35                  40                  45
Leu Asp Arg Arg Gly Met Arg Val Leu Ala Ala Cys Arg Lys Glu Glu
     50                  55                  60
Gly Ala Glu Glu Leu Arg Arg Lys Thr Ser Glu Arg Leu Glu Thr Val
```

```
                65                  70                  75                  80
Ile Leu Asp Val Thr Lys Thr Glu Asn Ile V al Ala Ala Thr Gln Trp
                    85                  90                  95
Val Lys Glu Arg Val Gly Asn Arg Gly Leu T rp Gly Leu Val Asn Asn
                    100                 105                 110
Ala Gly Ile Ser Val Pro Ser Gly Pro Asn G lu Trp Met Lys Lys Gln
                    115                 120                 125
Asp Phe Ala Ser Val Leu Asp Val Asn Leu L eu Gly Leu Ile Glu Val
                    130                 135                 140
Thr Leu Ser Met Leu Pro Leu Val Arg Lys A la Arg Gly Arg Val Val
145                 150                 155                 160
Asn Val Ser Ser Ile Leu Gly Arg Val Ser L eu Gly Gly Ser Gly Gly
                    165                 170                 175
Tyr Cys Ile Ser Lys Tyr Gly Ile Glu Ala P he Ser Asp Ser Leu Arg
                    180                 185                 190
Arg Asp Val Arg Tyr Phe Gly Val Lys Val A la Ile Ile Glu Pro Gly
                    195                 200                 205
Phe Phe Leu Thr Gly Met Ala Ser Ser Ala A rg Leu Cys Ser Asn Ile
210                 215                 220
Gln Met Leu Trp Asp Gln Thr Ser Ser Glu M et Arg Glu Ile Tyr Gly
225                 230                 235                 240
Glu Lys Tyr Leu Ala Ser Tyr Leu Lys Asn L eu Asn Glu Leu Asp Gln
                    245                 250                 255
Arg Cys Asn Lys Asp Leu Ser Val Val Thr A sp Cys Met Glu His Ala
                    260                 265                 270
Leu Thr Ala Cys His Pro Arg Thr Arg Tyr S er Ala Gly Trp Asp Ala
                    275                 280                 285
Lys Leu Phe Phe Thr Pro Leu Ser Tyr Leu P ro Thr Phe Leu Val Asp
                    290                 295                 300
Ala Leu Leu Tyr Trp Thr Ser Pro Lys Pro A sp Lys Ala Leu
305                 310                 315

(2) INFORMATION FOR SEQ ID NO:39:

(i) SEQUENCE CHARACTERISTICS:
        (A) LENGTH: 318 mino acids
        (B) TYPE: amino acid
        (D) TOPOLOGY: linear (xi) SEQUENCE DESCRIPTION: SEQ ID NO:39:

Met Trp Leu Pro Leu Leu Leu Gly Ala Leu L eu Trp Ala Val Leu Trp
                    5                   10                  15
Leu Leu Arg Asp Arg Gln Ser Leu Pro Ala S er Asp Ala Phe Ile Phe
                    20                  25                  30
Ile Thr Gly Cys Asp Ser Gly Phe Gly Arg L eu Leu Ala Leu Gln Leu
                    35                  40                  45
Asp Gln Lys Gly Phe Gln Val Leu Ala Gly C ys Leu Thr Pro Ser Gly
                    50                  55                  60
Ala Glu Asp Leu Gln Gln Met Ala Ser Ser A rg Leu His Thr Thr Leu
65                  70                  75                  80
Leu Asp Ile Thr Asp Pro Gln Asn Val Gln G ln Val Ala Lys Trp Val
                    85                  90                  95
Lys Thr Arg Val Gly Glu Thr Gly Leu Phe G ly Leu Val Asn Asn Ala
                    100                 105                 110
Gly Val Ala Gly Ile Ile Gly Pro Thr Pro T rp Leu Thr Gln Asp Asp
```

```
                    115                 120                      125
        Phe Gln Arg Val Leu Ser Val Asn Thr Leu Gly Pro Ile Gly Val Thr
                130                 135                 140

Leu Ala Leu Pro Leu Leu Gln Gln Ala Arg Gly Arg Val Val Asn
        145                 150                 155                 160

Ile Thr Ser Val Leu Gly Arg Ile Ala Ala Asn Gly Gly Gly Tyr Cys
                        165                 170                 175

Val Ser Lys Phe Gly Leu Glu Ala Phe Ser Asp Ser Leu Arg Arg Asp
                    180                 185                 190

Met Ala Pro Phe Gly Val Gln Val Ser Ile Val Glu Pro Gly Phe Phe
                    195                 200                 205

Arg Thr Pro Val Thr Asn Leu Glu Ser Leu Glu Ser Thr Leu Lys Ala
                    210                 215                 220

Cys Trp Ala Arg Leu Pro Pro Ala Ile Gln Ala His Tyr Gly Glu Ala
        225                 230                 235                 240

Phe Leu Asp Thr Tyr Leu Arg Val Gln Arg Arg Ile Met Asn Leu Ile
                        245                 250                 255

Cys Asp Pro Glu Leu Thr Lys Val Thr Ser Cys Leu Glu His Ala Leu
                    260                 265                 270

Thr Ala Arg His Pro Arg Thr Arg Tyr Ser Pro Gly Trp Asp Ala Lys
                    275                 280                 285

Leu Leu Trp Leu Pro Ala Ser Tyr Leu Pro Ala Arg Val Val Asp Ala
                    290                 295                 300

Val Leu Thr Trp Ile Leu Pro Arg Pro Ala Gln Ser Val Ser
        305                 310                 315
```

(2) INFORMATION FOR SEQ ID NO:40:

(i) SEQUENCE CHARACTERISTICS:
        (A) LENGTH: 21 base pairs
        (B) TYPE: nucleic acids
        (C) STRANDEDNESS: single
        (D) TOPOLOGY: linear (xi) SEQUENCE DESCRIPTION: SEQ ID NO:40:

TAGCTGGTAT CATCGGGCCC A                                            21

(2) INFORMATION FOR SEQ ID NO:41:

(i) SEQUENCE CHARACTERISTICS:
        (A) LENGTH: 19 base pairs
        (B) TYPE: nucleic acids
        (C) STRANDEDNESS: single
        (D) TOPOLOGY: linear (xi) SEQUENCE DESCRIPTION: SEQ ID NO:41:

AGAAACCAGG CAGCACTGG                                               19

(2) INFORMATION FOR SEQ ID NO:42:

(i) SEQUENCE CHARACTERISTICS:
        (A) LENGTH: 18 base pairs
        (B) TYPE: nucleic acids
        (C) STRANDEDNESS: single
        (D) TOPOLOGY: linear (xi) SEQUENCE DESCRIPTION: SEQ ID NO:42:

CACGTGGAGA TCCGCCAG                                                18

(2) INFORMATION FOR SEQ ID NO:43:

(i) SEQUENCE CHARACTERISTICS:
(A) LENGTH: 29 bas e pairs
(B) TYPE: nucleic acid s
(C) STRANDEDNESS: sin gle
(D) TOPOLOGY: linear (xi) SEQUENCE DESCRIPTION: SEQ ID NO:43:

ACGTGGATCC CCGCCTTCAT TCCCGAACA                              29

(2) INFORMATION FOR SEQ ID NO:44:

(i) SEQUENCE CHARACTERISTICS:
(A) LENGTH: 24 bas e pairs
(B) TYPE: nucleic acid s
(C) STRANDEDNESS: sin gle
(D) TOPOLOGY: linear (xi) SEQUENCE DESCRIPTION: SEQ ID NO:44:

TGGTATCGTG GAAGGACTCA TGAC                                   24

(2) INFORMATION FOR SEQ ID NO:45:

(i) SEQUENCE CHARACTERISTICS:
(A) LENGTH: 24 bas e pairs
(B) TYPE: nucleic acid s
(C) STRANDEDNESS: sin gle
(D) TOPOLOGY: linear (xi) SEQUENCE DESCRIPTION: SEQ ID NO:45:

ATGCCAGTGA GCTTCCCGTT CAGA                                   24

(2) INFORMATION FOR SEQ ID NO:46:

(i) SEQUENCE CHARACTERISTICS:
(A) LENGTH: 21 bas e pairs
(B) TYPE: nucleic acid s
(C) STRANDEDNESS: sin gle
(D) TOPOLOGY: linear (xi) SEQUENCE DESCRIPTION: SEQ ID NO:46:

GCTGGTCACC TTCGTTAGTT C                                      21

ISOLATED PROTEINS HAVING RETINOL DEHYDROGENASE ACTIVITY, AND WHICH ASSOCIATE WITH RETINOL BINDING RECEPTORS

RELATED APPLICATIONS

This application is a continuation-in-part of Ser. No. 08/729,594, filed on Oct. 11, 1996, which is a continuation-in-part of Ser. No. 08/562,114, filed Nov. 22, 1995, now U.S. Pat. No. 5,972,646 which is a continuation-in-part of Ser. No. 08/375,962, filed on Jan. 20, 1995, now U.S. Pat. No. 5,731, 195 which is a continuation-in-part of copending application Ser. No. 08/258,418, filed on Jun. 10, 1994, now abandoned. All of these applications are incorporated by reference.

FIELD OF THE INVENTION

This invention relates to proteins having retinol dehydrogenase activity, such as 9-cis, 11-cis or 13-cis retinol dehydrogenase activity, or trans retinol dehydrogenase activity and which form complexes with a specific portion of a membrane receptor for plasma retinol-binding protein (RBP) expressed, e.g., in retinal pigment epithelium (RPE), and, more specifically; proteins having cis retinol dehydrogenase activity, such as 9 or 11-cis retinol dehydrogenase activity, which form complexes with RBP-binding membrane proteins such as the 63 kDa RBP binding membrane protein found in RPE cells. The invention also involves isolation of the proteins, as well as nucleic acid molecules coding p32 or complementary to coding sequences therefor, in addition to various applications of these materials.

BACKGROUND OF THE INVENTION

Retinoids (vitamin A-derivatives) have important physiological functions in a variety of biological processes. During embryonic growth and development, as well as during growth and differentiation of adult organisms, retinoids act as hormones and participate in the regulation of gene expression in a number of cell types. See Lied et al. Trends Genet., 17:427–433 (1992). It is believed that these effects are mediated through two classes of nuclear ligand-controlled transcription factors, the retinoic acid receptors (RARs) and the retinoid X receptors (RXRs), Benbrook et al., Nature, 333:669–672 (1988); Brand et al., Nature, 332:850–853 (1988); Giguere et al., Nature, 330:624–629 (1987); Mangelsdorf et al., Nature, 345:224–229 (1990); Mangelsdorf, et al. Genes Dev. 6: 329–344 (1992); Petkovich et al. Nature 330:440–450 (1987); and Zelent et al., Nature 339:714–717 (1989).

Apart from their role as hormones in cellular growth and differentiation, retinoids are also involved in the visual process as the stereo isomer of retinaldehyde, 11-cis retinaldehyde, is the chromophore of the visual pigments. See, e.g. Bridges, *The Retinoids*,. Vol. 2, pp 125–176, Academic Press, Orlando, Fla., (1984).

Under normal physiological conditions most cells, both ocular and non-ocular, obtain all-trans retinol as their major source of retinoids. Despite the many different metabolic events taking place in different tissues, it is known that a common extracellular transport machinery for retinol has evolved. Specifically, in plasma, retinol is transported by plasma retinal binding protein (RBP). See Goodman et al., *The Retinoids*, Academic Press, Orlando Fla., Volume 2, pp. 41–88 (1984). The active derivatives of retinal, i.e., retinoic acid in non-ocular tissues and mostly 11-cis retinaldehyde for ocular tissues, are then generated by cellular conversion using specific mechanisms. To date, none of these mechanisms have been fully defined at the molecular level and several of the enzymes involved have only been identified by enzymatic activities. See Lion et al., Biochem. Biophys. Acta. 384:283–292 (1975); Zimmermann et al., Exp. Eye Res. 21:325–332 (1975); Zimmermann, Exp. Eye Res. 23:159–164 (1976) and Posch et al., Biochemistry 30:6224–6230 (1991).

Polarized retinal pigment epithelial cells (RPE) are unique with regard to retinoid uptake since all-trans retinol enters these cells via two different mechanisms. Retinol accumulated from RBP is taken up through the basolateral plasma membrane, while all-trans retinal, presumably taken up from the interstitial retinol-binding protein (IRBP) following bleaching of the visual pigments, may enter through the apical plasma membrane. See Bok et al., Exp. Eye Res. 22:395–402 (1976); Alder et al., Biochem. Biophys. Res. Commun. 108:1601–1608 (1982); Lai et al., Nature 298:848–849 (1982); and Inu et al., Vision Res. 22:1457–1468 (1982).

The transfer of retinol from RBP to cells is not fully understood. In a number of cell types, including RPE, specific membrane receptors for RBP have been identified, which is consistent with a receptor-mediated uptake mechanism for retinol. For example, isolated retinol binding protein receptors, nucleic acid molecule coding for these receptors and antibodies binding to the receptor have been taught, in references relating to the first of the two mechanisms. See Bavik et al., J. Biol. Chem. 266:14978–14985 (1991); Bavik, et al. J. Biol. Chem. 267:23035–23042 1992; Bavik et al., J. Biol. Chem. 267:20–540–20546 (1993); and copending U.S. Application Ser. No. 083,539 and International Publication WO 93/23538, all of which are incorporated by reference herein. See also Heller, J. Biol. Chem. 250:3613–3619 (1975); and Bok et al., Exp. Eye Res. 22:395–402 (1976).

Retinol uptake on the apical side of the RPE for the regeneration of 11-cis retinaldehyde is less well characterized. Regardless of the origin of all-trans retinol, however, the synthesis and apical secretion of 11-cis retinaldehyde seems to be the major pathway for accumulated retinol in the RPE. At present, it is not known whether similar mechanisms are used with regard to cellular retinol uptake through the basolateral and the apical plasma membranes. Available data do show that functional receptors for RBP are exclusively expressed on the basolateral plasma membrane of RPE-cells. Bok et al., Exp. Eye Res. 22:395–402 (1976).

It is also known that pigment RPEs express a 63 kDa protein (p63). This molecular weight, and all others, is by the refernce to SDS-PAGE, unless stated otherwise. It has also been shown by chemical cross-linking that this protein may be part of an oligomeric protein complex which functions as a membrane receptor for plasma retinol-binding protein (RBP) in RPEs, or a component of the retinoid uptake machinery in RPE cells. See Bavik et al, J. Biol. Chem. 266:14978–14875 (1991); Bavik et al., J. Biol, Chem. 267:23035–23042 (1992), and U.S. Application Ser. No. 083,539 and PCT application WO93/23538. The p63 protein has been isolated and the corresponding cDNA cloned. See Bavik et al., J. Biol. Chem. 267:20540–20546 (1993). Homologous molecules which bind to retinol binding proteins have been identified in other tissues, such as the liver. However, there is nothing in these references suggesting the existence of the protein which is a feature of this invention.

SUMMARY OF THE INVENTION

In accordance with this invention, proteins having retinol dehydrogenase activity which have a molecular weight of from about 30 to about 36 kD, as determined by SDS-PAGE, have now been discovered. These proteins form oligomeric protein complexes with the previous described components of the membrane receptor for RBP, such as the p63 molecule discussed supra. Also disclosed are nucleic acid molecules which code for these proteins. Sequence analysis shows that the proteins belong to the family of short chain alcohol dehydrogenases, and exhibit cis retinal dehydrogenase activity such as 9 or 11-cis retinol activity, the enzyme which catalyzes the stereospecific conversion of 9 and/or 11-cis-retinol into corresponding retinaldehydes in the presence of cofactor NAD+. In addition, other members of the short chain alcohol dehydrogenase family are disclosed, which have all trans-retinol dehydrogenase activity.

As will be shown, the proteins have many important uses. For example, owing to its membrane bound retinol dehydrogenase activity, which catalyzes the conversion of cis-retinols to cis-retinaldehydes, a major metabolic step in retinoid metabolism in RPE-cells, retinoid accumulation and metabolism which may lead to retinitis pigmentosa, may be directly or indirectly tied to the presence of these proteins, and/or their activation or inhibition. As the proteins have also been found to be members of the short chain alcohol dehydrogenase super family, many known alcohol dehydrogenase inhibitors (and activators) are available to develop activity assays, and thus diagnostic materials for retinol uptaken and retinoid metabolism.

Also a part of this invention are nucleic acid molecules which encode mammalian forms of the proteins, such as the human, bovine, and murine forms. Also a part of the invention are probes, based upon the nucleotide sequences described herein.

These and other aspects of this invention are more fully discussed in the following Detailed Discussion with accompanying drawings.

BRIEF DESCRIPTION OF THE DRAWINGS

FIG. 3 illustrates the nucleotide sequence of pλ321 and the deduced amino acid sequence of the protein of FIGS. 2A and 2B, with the partial amino acid sequences determined from peptides isolated from the trypsin digested protein (SEQ ID No:10).

FIG. 4 illustrates amino acid sequence alignments of the protein and some related proteins belonging to the family of short-chain alcohol dehydrogenases (SEQ ID NOS. 10, 11, 12 and 13).

DETAILED DISCUSSION OF PREFERRED EMBODIMENTS

Figure 1A:
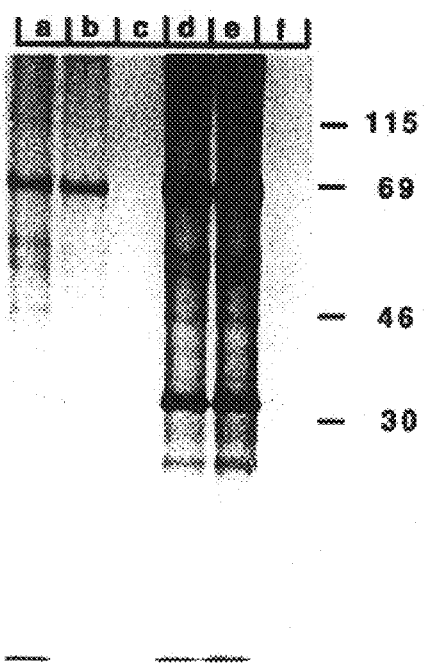
FIG. 1A shows SDS-PAGE analysis of radiolabeled protein from RPE-membranes and immunoprecipatation with mAb A52 against p63.

It is known that plasma retinol binding protein (RBP) can be chemically cross-linked to a high molecular weight complex of a 63 kDa protein (p63) receptor of retinal pigment epithelium membranes (RPE), forming an RBP-RBP receptor complex with elution properties of globular proteins of similar sizes having apparent molecular weights of approximately $M_r$ 150,000 and 450,000. See Bavik et al, J. Biol. Chem. 266:14978–14875 (1991), and Bavik et al., J. Biol. Chem. 267:23035–23042 (1992). The protein responsible for binding of RBP, expression of which is restricted to RPE, has been identified as a 63 kDa protein (p63). Through the generation of a monoclonal antibody A52 (mAb A52) to the 63 kDa protein which binds the RBP-RBP receptor complex and p63, and immunoaffinity chromatographic analysis, a majority of p63 is eluted as a monomer, with a significant portion of the protein found in positions corresponding to higher molecular weight species. This indicates that p63 exists in an oligomeric protein complex with other protein components. Bavik et al., J. Biol. Chem. 266:14978–14985 (1991), and Bavik et al, J. Biol. Chem. 267:23035–23042 (1992). Therefore, the following procedure was carried out to investigate the molecular characteristics of such oligomeric protein complexes, and whether p63 forms a complex with other proteins specific to RPE. The results show that a 32 kDa membrane associated protein referred to hereafter as p32 indeed forms a complex with p63.

EXAMPLE 1

Bovine RPE-cells were isolated and membrane fractions were prepared as described in Bavik et al, J. Biol. Chem. 266:14978–14875 (1991) incorporated by reference. RPE-membrane proteins were then solubilized in phosphate-buffered saline (PBS) (20 mM sodium phosphate, PH 7.2, containing 150 mM NaCl), containing 1% 3-[(3-cholamidopropyl) -dimethylammonio] -1-propane sulfonic acid (CHAPS) at 1 mg of total membrane protein/ml of buffer.

Remaining material was removed by ultracentrifugation at 100,000×g for 1 hour. Next, 500 ul aliquots of the solubilized membranes were subjected to gel filtration on a Sepharose 6 column equilibrated in PBS containing 1% CHAPS. The column was operated at a flow rate of 0.2 ml/min and 500 ul fractions collected. Proteins eluted in fractions corresponding to globular proteins of $M_r$ 150,000 to 400,000 were then radiolabelled with Na$^{125}$I using the well-known Chloramin T procedure. Non-incorporated $^{125}$I was removed by gel filtration on Sepahadex G-25 packed in a Pasteur pipette.

Aliquots of the radiolabelled proteins were then diluted in PBS containing 1% CHAPS and 1% bovine serum albumin and subsequently subjected to immunoprecipitation using the mAb A52 to p63 (5 ug per incubation) or using two polyclonal rabbit antisera to p63 (3 ul of serum per incubation) See Bavik et al., J. Biol. Chem. 267:23035–23042 (1992). Non-specific immunoprecipitation was monitored in parallel incubations using an unrelated mAb and preimmune rabbit serum. Fifty ul of a 50% slurry of protein A-Sepharose was added to the incubations for 30 minutes. The beads were subsequently carefully washed with PBS containing 1% CHAPS and the eluted material then prepared for SDS-PAGE analysis, which was carried out according to Blobel et al. J. Cell. Bio. 67:835–851 (1975).

Referring now to FIG. 1A, autoradiograms of the SDS-PAGE gels showed that both types of reagents reacted with p63, whereas the unrelated mAb or preimmune rabbit serum did not precipitate p63. In all lanes containing immunoprecipitated p63 there was an enrichment of a $M_r$ 32,000 protein. Since both mAb A52 and the rabbit antisera to p63 are highly specific for p63 (See, for example, Bavik et al., J. Biol. Chem. 267:23035–23042 (1992)), it can be concluded that the $M_r$ 32,000 protein (p32) coprecipitated in the aforesaid analysis by binding to p63. The analysis also identified a double band of $M_r$ 50,000–52,000 which precipitated along with p32 and p63 (FIG. 1 d, e).

EXAMPLE 2

Figure 1B:
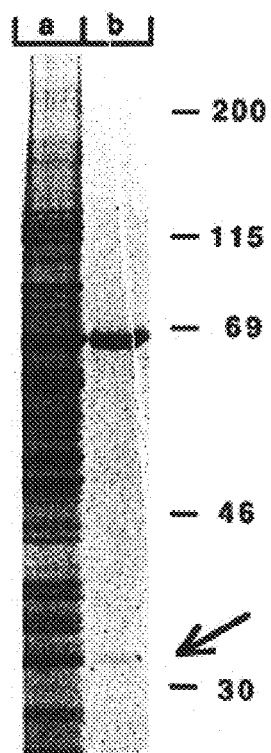
FIG. 1B shows SDS-PAGE analysis of RPE-membrane proteins bound and eluted through a mAb A52 immunoaffinity column, and the presence of a protein in accordance with the invention, in the eluted faction from the immunoaffinity column.

Experiments were then carried out to identify p32. Advantage was taken of the fact that p32 specifically interacts with p63 as shown supra. Thus, detergent solubilized RPE-membrane proteins were passed over an immunoaffinity column containing mAb A52. Referring now to FIG. 1B, lane b, following a washing procedure, bound proteins were eluted at high pH in a CHAPS-containing buffer, and SDS-PAGE analysis and Coomassie staining of the eluted fractions revealed p63 to be specifically retained and eluted from the immunoaffinity column. Further, a weekly stained band corresponding to p32 could be visualized in the eluate from the A52 column. As shown in FIG. 1B, a comparison of the total protein profile of solubilized RPE membranes and the eluted fraction from the A52 column show that the p32 protein is not efficiently retained therein. However, the appearance of p32 in the eluted fraction from the A52 column, but not in the eluted fraction from the column containing an unrelated Ig, indicate a specific interaction of p32 with p63. This result is consistent with previous immunoprecipitation data, and shows that p32 is complexed to p63 and is retained on the immunoaffinity column due to this complex formation.

Following identification of p32 as a component of a complex with p63 in RPE-membranes, the p32 protein itself was isolated by SDS-PAGE of eluted fractions of solubilized RPE-membranes from the A52 immunoaffinity column, as set forth below in Example 3.

EXAMPLE 3

RPE-membranes were solubilized in PBS containing 1% CHAPS as set out above and then incubated with mAb A52 Ig coupled to CNBr-activated Sepharose 4B beads (Pharmacia) in a Bio-Rad poly prep column (Bio-Rad) by end-over-end rotation at +4° C. Following a 2 hour incubation, the beads were allowed to settle and the column was quickly washed with 5 column volumes of PBS containing 1% CHAPS. Bound proteins were then eluted with 50 mM triethanolamine buffer (pH 11.2) containing 1% CHAPS. The pH of the eluate was quickly adjusted to 8.0 by the addition of 1 M Tris-HCl buffer containing 1% CHAPS. The eluted fractions were subjected to SDS-PAGE, and the separated proteins then visualized by Coomassie Blue staining. A band corresponding to p32 (SDS-PAGE, 32kDa), was found.

To determine the primary structure of p32)partial amino acid sequence analysis of the isolated protein was undertaken by first cutting out a portion of the aforesaid Coomassie stained band corresponding to approximately 2–5 ug of the 32kDa protein, then lyophilizing the gel piece to dryness. The gel was rehydrated in buffer containing modified trypsin and incubated to generate various peptides for extraction and analysis. A preferred procedure is set forth below in Example 4.

EXAMPLE 4

Coomassie stained bands containing the p32 protein from Example 2 were excised and treated according to Rosenfeld et al. Anal. Biochem. 15:173–179 (1992) with minor modifications. The gel pieces were washed twice for 30 min at 30° C. with 100 ul of 0.2 M ammonium bicarbonate buffer containing 50% acetonitrile and thereafter completely dried under a stream of nitrogen. The gel pieces were subsequently rehydrated with 5 ul of 0.2 M ammonium bicarbonate buffer containing 0.02% Tween 20 and 0.5 ug of modified trypsin. Trypsin was added from a stock solution prepared in 1 mM HCl. Rehydration was continued by the addition of 5 ul portions of the 0.2 M ammonium bicarbonate buffer until the gel pieces rehydrated to their original sizes. The rehydrated gel pieces were then incubated overnight at 30° C. Protease activity was inhibited by the addition of trifluoroacetic acid (TFA) to a final concentration of 1%. The supernatant was recovered and combined with two extracts made with 150 ul of 0.1% TFA in 60% acetonitrile. The organic phase was reduced, and the digest was subjected to HPLC using a reverse phase mRPC C2/C18 SC 2.1/10 column operated in a SMART system. The sample was eluted with a gradient of acetonitrile in 0.065% TFA and fractions containing discrete peptides were collected using the automatic peak fractionation option. Five of the identified peptides were selected for amino acid sequence analysis using an ABI 470A sequencer equipped with a model 120A PTH analyzer (applied Biosystems Inc. Foster City, Calif.). The results are set forth below in Table 1.

TABLE 1

Amino acid sequences determinations of
five peptides isolated from trypsin digested p32.

p321  L-V-E-A-V-L-A-E-V-L-P-K-P-A-Q-T-V-A (SEQ ID NO:1)
      (D)[a]     (W)            (Y)

P322  Y-S-P-G-W-D-A-K (SEQ ID NO: 2)

P323  T-P-V-T-N-L-E-T-L-E-D-T-L-Q-A (SEQ ID NO: 3)

P324  D-V-A-P-F-G-V (SEQ ID NO: 4)

P325  L-H-T-T-L-L-D-V-T-D-P-Q-S-I (SEQ ID NO: 5)

[a] The amino acid residues given within the parentheses are
the residues deduced from the cDNA sequence in the same
positions.

Protein SEQ ID NOS: 1–5 can be used alone or ligated to haptens by well known methods.

Next, to determine the complete primary structure of p32, four degenerative oligonucleotide mixtures, OM1–OM4, as set forth below in Table 2 were synthesized based on the amino acid sequences of the p321 and p323 sequenced peptides of Table 1. The procedure is as follows in Example 5.

EXAMPLE 5

Four degenerate oligonucleotide mixtures derived from peptides p321 and p323 were synthesized using well-known techniques. The two sense mixtures (OM1 and OM3) were derived from the N-terminal amino acids 1–5 of p321 and 2–6 of p323. The antisense mixtures (OM2 and OM4) were derived from amino acids 12–17 of p321 and 10–15 of p323. All nucleotide mixtures were synthesized with a 4 bp 5' extension and an Eco RI-site for subsequent cloning of the PCR products. The sequences of the oligonucleotide mixtures are set out below in Table 2, and the Eco RI-site is underlined. Positions containing all four bases are marked N.

PCR reactions were performed using a final concentration of 0.5 uM of the oligonucleotide mixtures in a 100 ul reaction. Taq polymerase was used. Following 30 cycles (2 minute at 95° C., 1 minute at 55° C. and 2 minute at 72° C.), aliquots of the reactions were analyzed on 4% GTG agarose gel containing 5 ug/ml of ethidium bromide.

Figure 2:
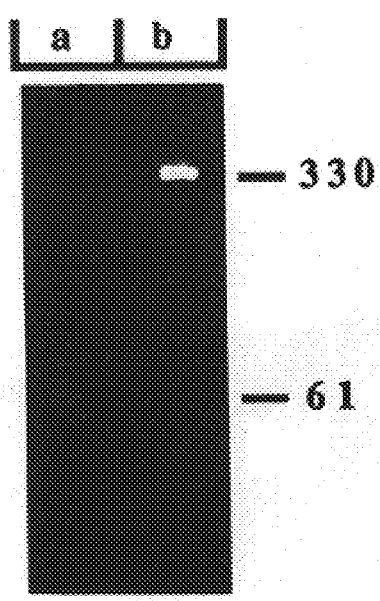
FIG. 2A shows visualization in agarose gel electrophoresis of a 61 bp PCR-amplified fragment using oligonucleotide mixtures OM1 and OM3, both derived from peptide 321 deduced from partial amino acid sequence determination of trypsin digested protein.
FIG. 2B shows visualization of a 330 bp PCR-amplified fragment using oligonucleotide mixtures OM2 and OM3, derived from peptides p323 and p321, respectively, as deduced from partial amino acid sequence determination of the trypsin digested protein of figure 2B.

As shown in FIG. 2A, amplifications using the oligo-nucleotide mixtures OM1 and OM2, both derived from peptide p321, resulted in an amplified 61 bp fragment. Amplifications using mixtures OM3–OM4 and OM1–OM4 failed to yield any products. Finally, as shown in FIG. 2B, amplification using OM3–OM2 resulted in an amplified 330 bp fragment.

Subsequent sequence analysis of the 61 bp and 330 bp fragments confirmed that cDNA sequences had been amplified which corresponded to the peptide sequences generated in the previous amino acid sequence analysis. Differences between the deduced amino acid sequences from amplified PCR fragments and the generated amino acid sequence of peptide p321 indicates the generation of specific probes suitable for the isolation of full length cDNA clones encoding p32.

To isolate a full length cDNA clone, an RPE-specific lambda ZAP-II cDNA library was screened with the 330 bp

TABLE 2

OM1:ACGT GAA TTC TN GTN GA(A,G)GCN GT (SEQ ID NO: 6)

OM2:ACGT GAA TTC AC NGT(T,C)TG NGC NGG(T,C)TT (SEQ ID NO: 7)

OM3:ACGT GAA TTC CCN GTN ACN AA(T,C) (C,T)T (SEQ ID NO: 8)

OM4:ACGT GAA TTC GC(T,C)TG NA(A,G)NGT(A,G)TC(T,C)TC (SEQ ID ND: 9)

Single stranded "complementary" cDNA from reverse transcribed RPE mRNA and four combinations of the above-described degenerate nucleotide mixtures were employed in polymerase chain reactions (PCR) using a standard procedure. Following the amplification procedure, aliquots of the PCR reaction products were analyzed by agarose gel electrophoresis. The procedure is set out below in Example 6.

EXAMPLE 6

To carry out the PCR amplifications, first strand cDNA was synthesized by standard procedures using avian myelostosis virus reverse transcriptase. Twenty ug of total RNA from isolated RPE-cells were used and the reaction was primed with oligo (dT) 15. Aliquots corresponding to 2 ug of total RNA was used in each subsequent PCR reaction. The fragment as the probe. Five independent lambda clones were isolated from approximately 200,000 clones, and subcloned by in vivo excision. The cDNA clone pλ321 contained the longest insert, (approximately 1.1 Kb), and was selected for use in further studies.

Both strands of pλ321 were fully sequenced with the insert being 1104 bp long, excluding linkers used to prepare the cDNA library. The procedure is set out below in Example 7.

EXAMPLE 7

The amplified products using OM1–OM2 (61 bp) and OM3–OM2 (330 bp) were digested with EcoRI, gel purified and cloned into EcoRI-cut vector pBS. The $^{32}$P-labelled 330 bp fragment was used to screen an RPE-specific λZAP II cDNA library as previously described by Bavik et al., J. Biol. Chem. 267:20540–20546 (1993), incorporated by reference. Five positive λ clones were isolated and the inserts were subcloned in pBluescript by in vivo excision following the manufacturer's instructions. Clone pλ321 contained an insert of 1.1 Kb, and both strands were fully sequenced using Sequenase with T3, T7 or M13 universal primers or with internal primers.

The nucleotide sequence of pλ321 and the predicted amino acid sequence of p32 are shown in FIG. 3 (SEQ ID NO: 10). Nucleotides are numbered on the left and amino acid residues on the right. Amino acid 1 is initial methionine ("Met").

As shown in FIG. 3, the 1.1 kbp insert contains one long open reading frame encoding 318 amino acid residues with a calculated mass of 35,041D. The first methionine residue lies in a good context according to the Kozak rules for transcription initiation and is likely to be the initiation codon. See Kozak, Cell, 44:283–292 (1986). This inference is strengthened by the fact that in vitro translation of synthetic mRNA transcribed from pλ321 gives rise to a $M_r$ 32,000 protein (SDS-PAGE analysis), as set out below, but there is no stop codon in frame in the upstream 35 bp 5'-untranslated region of the cDNA. As also shown in FIG. 3, the 100 bp 3'-untranslated region ends with a putative polyA-tract, and a polyA-signal was identified in-the upstream sequence (bp 1104–1110).

The deduced amino acid sequence pλ321 and the amino acid sequences of the five generated tryptic peptides (Table 1) differ in only 3 positions out of the 62 residues available for a comparison. All 3 differences are found in the peptide p321 but the nucleotide sequence in this region of a second cDNA clone (pλ324) is identical to that of pλ321. This indicates that the amino acid sequence determination of peptide p321 was probably incorrect although it cannot be excluded that the differences are due to the presence of different alleles of p32. These data demonstrate that pλ321 contains the complete coding-region of p32.

Again, referring to FIG. 3, a consensus sites for N-linked glycosylation (amino acid residues N-I-T) could be found in the deduced amino acid sequence at position 160–162.

Additionally, it has been found that p32 shows sequence similarities to short-chain alcohol dehydrogenases. Referring now to FIG. 4 a search through the Swissprot protein data base revealed that p32 is structurally related to several previously sequenced proteins. It is most closely related to a mitochondrial matrix dehydrogenase, the D-β-hydroxybutyrate dehydrogenase (BDH) Churchill et al; Biochem. 31:3793–3799 (1992) and shows less but significant similarities to two other proteins, the 3-oxoacy[acyl carrier protein] reductase from *E. coli* (Rawlings et al., J. Biol. Chem. 267-5751–5754 (1992)) and the human estradiol 17 β-dehydrogenase (Peltoketo et al., FEBS Lett., 239:73–77 (1988) and Leu et al., Mol. Endocrinol. 3:1301–1309 (1989)). All the related proteins fall into the protein superfamily of short-alcohol dehydrogenases. This protein superfamily comprises approximately 50 different proteins (Persson et al, Eur. J. Biochem, 200:537–593 (1991)). The overall sequence homology between p32 and BDH is around 39%. The level of homology to the *E. coli* reductase and to the estradiol 17-β-dehydrogenase is lower (31% and 33%, respectively).

Optimal multiple alignment identified several conserved regions shared by p32 and the most closely related proteins (boxed areas in FIG. 4). The first region involving residues 63–69 (using the numbering in FIG. 4) which displayed the conserved motif G-X-X-X-G-X-G is believed to be the binding site for cofactors NAD, NADP or their reduced forms. Another conserved region is found between residues 148–153 (consensus sequence L-V-N-N-A-G) but no functional characteristics have yet been attributed to that sequence motif. The sequence motif Y-X-X-X-K, thought to be the active site, is the most highly conserved motif in short-chain alcohol dehydrogenases and is present in p32 residues 175–179, See Persson et al., Eur. J. Biochem, 200:537–593 (1991). These similarities demonstrate that p32 exhibits several features of a functional short-chain alcohol dehydrogenase.

Figure 5:
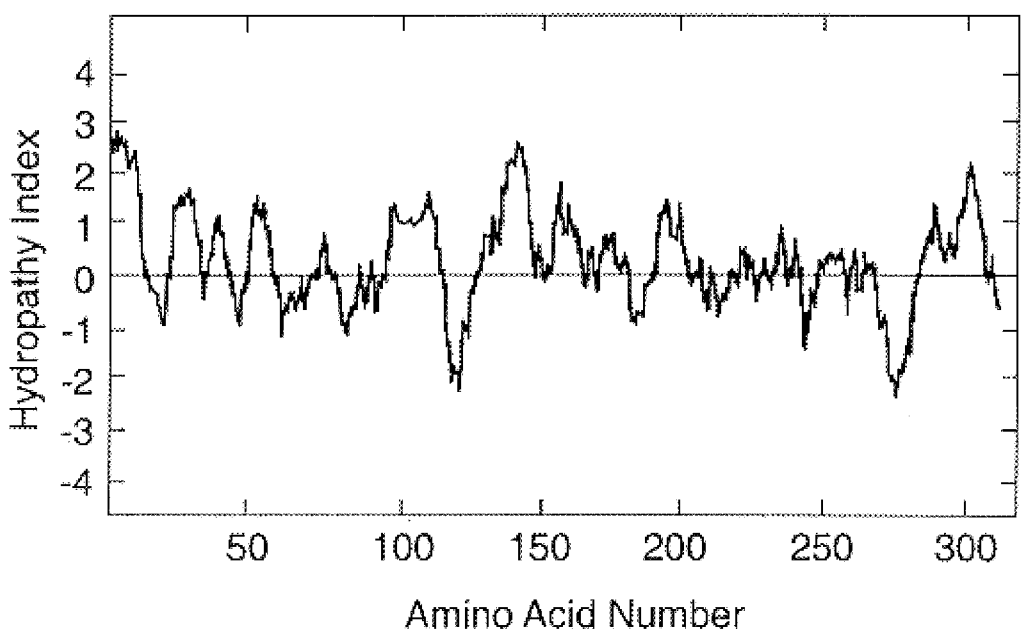
FIG. 5 illustrates analysis of the amino acid sequence of the protein under investigation.

As shown in FIG. 5, hydropathy analysis of the amino acid sequence of p32 reveals several hydrophobic stretches, indicating that p32 is a membrane-associated protein. The first 18 amino acids are hydrophobic, and this region has characteristics of a classical signal sequence. However, a consensus site for signal peptidase cleavage could not be identified. See Von Heijne, Nucl. Acid Res., 14:4683–4690 (1986). The amino acids between residues 130 to 150 are hydrophobic and there is a relatively long hydrophobic stretch near the C-terminus of the protein. Thus, p32 a displays several hydrophobic regions which are potential membrane spanning segments. In light of the homology to the family of short-chain alcohol dehydrogenases as shown above, it is likely that the central hydrophobic region of p32 (residues 130–150) is not used as a membrane anchor. Instead, both the N-terminal and the C-terminal regions are potential membrane anchoring domains.

To determine the mode of interaction of p32 with membranes, p32 was synthesized by in vitro translation using a reticulocyte lysate system with mRNA transcribed from linearized pλ321. The procedure is set out in Example 8 below.

EXAMPLE 8

Expression of P32 by in Vitro Translation

In vitro transcribed mRNA encoding p32 was synthesized from linearized pλ321 using T7 RNA polymerase. In vitro translation reactions were carried out using nuclease treated rabbit reticulocyte lysate following the manufacturer's instructions. Fifty ng of mRNA was included in each reaction, with or without the addition of dog pancreatic microsomes. To isolate membrane inserted p32, the microsomes were collected by centrifugation at 10 12,000×g for 10 min at 4° C. The microsomes were carefully resuspended in PBS and recentrifugated.

Figure 6:
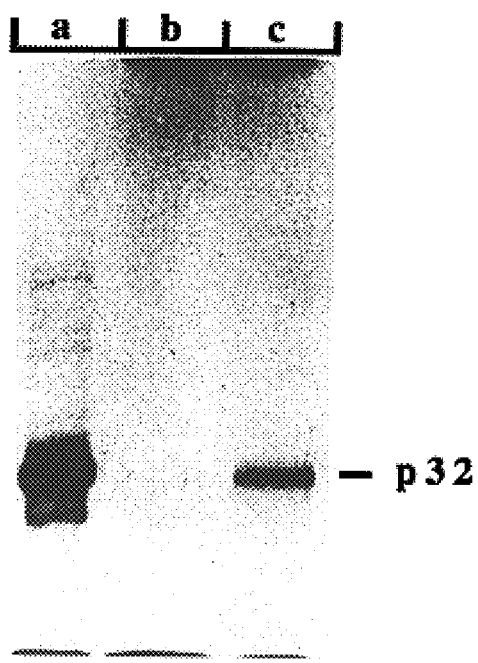
FIG. 6 illustrates membrane interaction of p32 synthesized in vitro.
Figure 7:
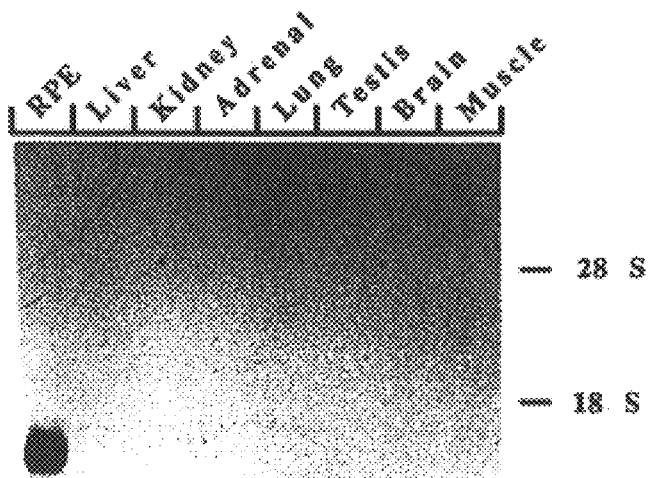
FIG. 7 illustrates the restricted expression of transcripts corresponding to the DNA encoding the protein.

As shown in FIG. 6, translation in the presence of dog pancreatic microsomes showed that p32 becomes almost quantitatively membrane associated and migrates as a $M_r$ 32,000 species in SDS-PAGE. Translation in the absence of acceptor membranes similarly yields a $M_r$ 32,000 protein. These data indicate that the N-terminal hydrophobic sequence acts as a signal sequence but it is not removed by the signal peptidase, and such supports the previous observation that a consensus site for signal peptidase cleavage could not be identified in the deduced primary sequence.

The tissue expression of p32 was analyzed by Northern blotting analyses using total RNA isolated from bovine RPE, liver, kidney, adrenal, lung, testis, brain and muscle. The procedure is set out in Example 9.

EXAMPLE 9

Northern Blot Analyses

Twenty ug of total RNA-isolated from a number of tissues was electrophoresed on a 1% agarose under denaturing conditions and transferred to a Hybond-N nylon filter. The filter was hybridized with $^{32}$P-labelled full length cDNA encoding p32 under stringent conditions. The details of the isolation of total RNA, hybridization conditions and washing procedure were identical to those previously described in Bavik, et al., J. Biol. Chem. 267:20540–20546 (1993).

Hybridization at high stringency with the 1.1 Kb insert of pλ321 as the probe, revealed abundant expression of transcripts corresponding to p32 only in RPE but not at a detectable level in several other tissues. The size of the major transcript was 1.4 kb but other less abundant transcripts could be visualized after prolonged exposure of the filters both in RPE as well as in other tissues.

EXAMPLE 10

Expression of p32 in COS-cells and Enzymatic Analysis of the Properties of Recombinant P32.

p32 was first expressed in COS-cells using a eukaryotic expression vector, and then microsome fractions from transfected cells and control cells were subjected to immunoblotting analysis to verify the expression of p32 at the desired levels, as follows:

Specifically, the EcoRI—insert of pλ321 was cloned into the EcoR1-digested eucaryotic expression vector pSG5. See Green et al., Nucl. Acid Res. 16:39 (1988). COS-cells were maintained in Dulbecco's minimal essential medium supplemented with 10% fetal bovine serum, 2mM glutamine and antibiotics. The cells were seeded into 60 mm petri dishes ($4 \times 10^5$ cells per dish) and transfected with 5 ug of plasmid per dish using DEAE dextran. Control cells were transfected with equal amounts of the parental vector alone. After treatment with 10% DMSO for 2 minutes, the cells were incubated for 72–96 hours, and then harvested by scraping the dishes with a rubber policeman, and the cells thereafter collected by low speed centrifugation. The collected cell pellets were next resuspended in hypotonic buffer (10 mM Tris-HCl, pH 7.5 containing 1mM phenyl-methylsufonyl fluoride), put on ice for 20 minutes, and then homogenized using a Dounce homogenator. Unbroken cells and debris were removed by centrifugation (3000×g)for 15 minutes. Microsomes were subsequently collected by ultracentrifugation at 100,000×g for 1 hour; membrane pellets were stored at −80° C. until further analyzed.

Antisera to p32 were generated by injecting rabbits with p32 (amino acid residues 19–318) expressed as a fusion protein with GST. The bacterial expression vector PGEX 2T was used and GST-fusion protein was induced and purified, as recommended by the supplier (Pharmacia). Each rabbit received a subcutaneous injection of 75 ug of fusion protein emulsified in Freunds complete adjuvant. The rabbits were boostered with 50 ug of fusion protein emulsified in Freunds incomplete adjuvant every second week. Blood was collected every second week. The immune rabbit sera were passed over a column containing GST fusion-protein immobilized on CNBr activated Sepharose beads. Bound Ig was eluted with 0.1 M sodium citrate buffer (pH 3.0), containing 0.5 M NaCl. To remove Ig to the GST portion of the fusion protein, the eluted Ig was similarly incubated with GST-coupled Sepharose beads and the unbound Ig fraction was used. For immunoblot analysis of the over expressed protein, the Ig was used at a concentration of 1 ug per ml. The details of the immunoblotting procedure are described in detail in Bavik et al., J. Biol. Chem., 267:23035–23042 (1992) the disclosure of which is herein incorporated by reference.

Figure 8A:
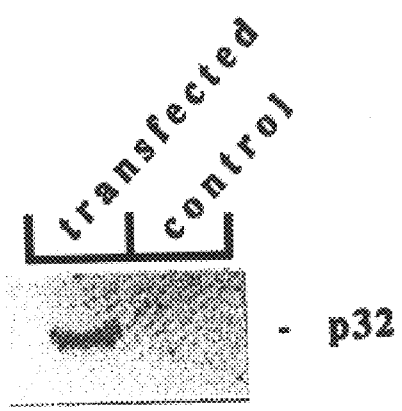
FIG. 8A illustrates expression of the protein in transfected cells for further enzymatic activity analysis of 11-cis retinol dehydrogenase activity.

As shown in FIG. 8A, the above procedure resulted in expression of p32 in cells transfected with the recombinant expression vector, but not in control cells that were mock transfected.

Next, some of the enzymatic properties of p32 expressed in COS-cells were determined in a manner similar to that as described in the study of 11-cis-retinol dehydrogenase activity in microsomal fractions of RPE cells. See Saari et al., Anal. Biochem 213:28–13226 (1993).

In particular, enzymatic activity of p32 was assayed by incubating the microsomal fractions from the aforementioned transfected cells, and from control cells lacking p32, with varying combinations of the different stereo isomeric substrates, i.e., 11-cis-retinol or all-trans-retinol, in the presence of either cofactor NAD+ or NADP.

To prepare the substrate, 11-cis retinol was synthesized from 11-cis-retinaldehyde using sodium borohydride, as set forth in Heller et al., J. Biol. Chem. 248:6308–6316 (1973), and stored under argon at 80° C. HPLC analysis confirmed the quantitative reduction of 11-cis-retinaldehyde to 11-cis-retinol, and all manipulations with the retinoids were done under subdued lighting conditions.

To assay for p32 activity in transfected cells, the final concentration of 11-cis-retinol and all-trans-retinol (obtained from Sigma Chemical Co.) in the incubations was reduced to 100 uM. Twenty ug of total membrane protein from COS-cells expressing p32 or from control cells were used in each incubation, and thereafter a 30 minute incubation at 37° C. in the presence or absence of NAD+ or NADP followed. Reaction mixtures were then extracted with n-hexane, and organic phases removed and dried under argon. The dried organic phases were then separately dissolved in ethanol and aliquots were analyzed on a normal phase silica HPLC column developed with n-hexane containing 4% dioxane at 1 ml per minute. See Saari et al. J. Biol. Chem. 257:13329–13333 (1982). Effluent was monitored at 330 nm. Under these conditions, 11-cis-retinaldehyde and 11-cis retinol eluted at 7 minutes and 22.5 minutes, respectively, and all-trans-retinaldehyde and all-trans retinol eluted at 8 minutes and 23 minutes, respectively.

Figure 8B:
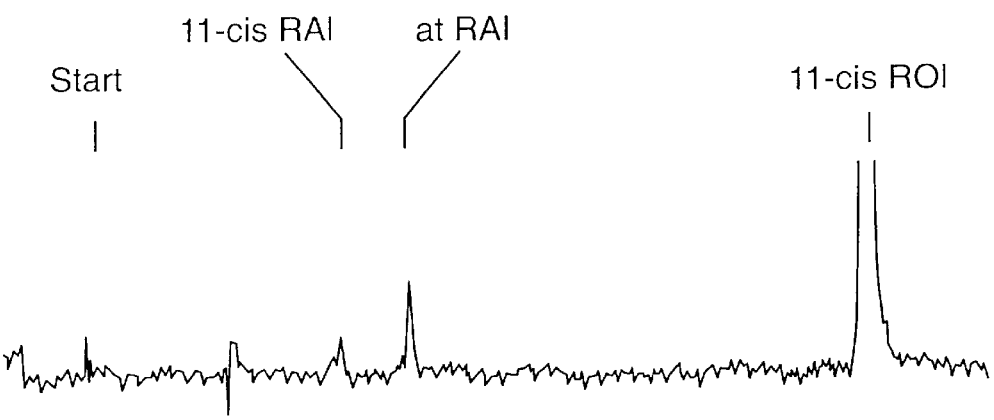
FIG. 8B illustrates the expression of 11-cis retinol dehydrogenase activity in the presence of NAD+ as indicated by the formation of 11-cis retinaldehyde.

As indicated in FIG. 8B, the aforementioned HPLC analysis shows that fractions from transfected cells containing p32 expressed 11-cis-retinol dehydrogenase protein which was active in the presence of NAD+, as indicated by the formation of 11-cis-retinaldehyde. A second peak in the chromatogram is all-trans retinaldehyde; however, control incubations with 11-cis retinaldehyde, in the absence of cellular membranes, show that, under the test procedure employed, a large amount of 11-cis retinaldehyde isomerizes to all-trans retinaldehyde. This indicates that the appearance of all-trans retinaldehyde is due to its generation during the incubation process used and extraction procedures, and is not an enzymatic reaction product. Further, incubations with all-trans retinol with cells containing p32 verify the stereo specificity of the enzyme, as no significant formation of all-trans retinaldehyde is detected.

Figure 8C:
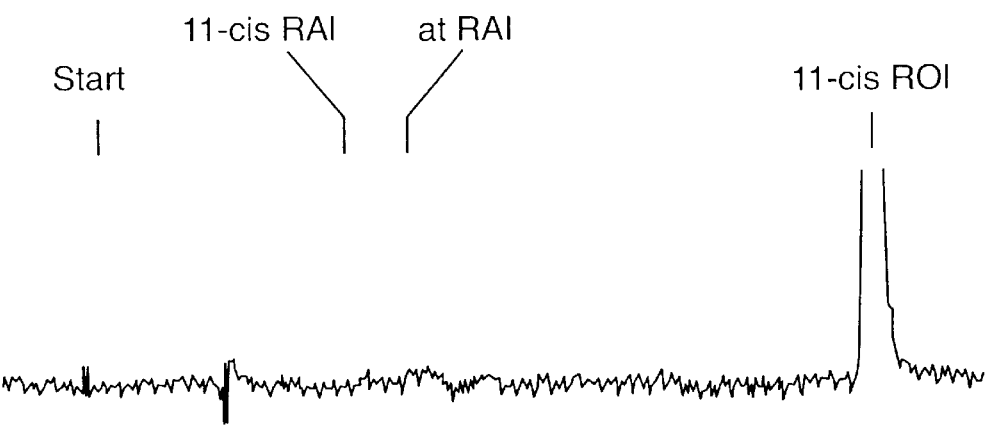
FIG. 8C illustrates the lack of 11-cis-retinol dehydrogenase activity in the presence of cofactor NADP.

As shown in FIG. 8C, p32 is not enzymatically-active in the presence of cofactor NADP.

Figure 8D:
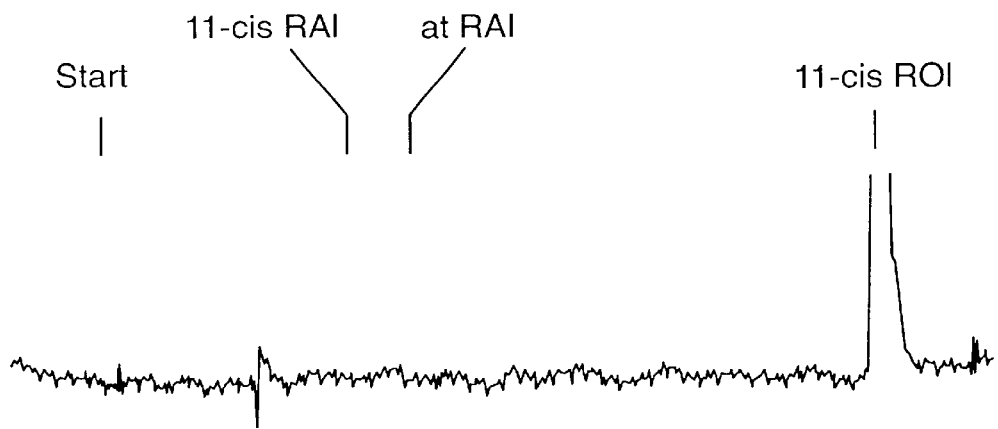
FIG. 8D illustrates control cells not expressing the protein which lack the ability to oxidize 11-cis-retinol into 11-cis-retinaldehyde.

In FIG. 8D, assays of the control cells not expressing p32 show that these do not oxidize 11-cis-retinol into 11-cis-retinaldehyde.

Therefore, the above shows conclusively that p32 is a stereo specific 11-cis-retinol dehydrogenase, which relies on NAD+ as its cofactor. In further experiments, it was established that the p32 molecule also has 9-cis retinol dehydrogenase activity.

EXAMPLE 11

Following the work described supra, using bovine materials, additional experiments were carried out to isolate and to clone a human sequence.

A cDNA library from human eye, in λgt11 was purchased from a commercial supplier (i.e., Clontech). The bovine cDNA described supra, i.e., SEQ ID NO: 10, was used as a probe. The cDNA was $^{32}$[P] dCTP labelled by random priming to a high specific activity (about $10^9$ cpm/μg of DNA).

The labelled bovine cDNA was then used to probe the human cDNA library. Conditions were as follows: hybridization in 6×SSC, 0.5% SDS, 5×Denhardt's solution, 25% formamide, at 68° C., with 100 μg/ml of salmon sperm DNA, followed by four washes of 2×SSC, 0.5% SDS, at 65° C., for 30 minutes each, and then a final wash at 2×SSC at 42° C. for 30 minutes.

When a positive cDNA was found, the insert (i.e., the cDNA), was excised following the manufacturer's instructions, and then subcloned into the commercially available vector pBluescript. The sequence of the insert was then determined, using well known methods. The sequence of 1128 nucleotides is set forth at SEQ ID NO: 14. The corresponding amino acid sequence of 318 residues is se forth in SEQ ID NO:15.

EXAMPLE 12

In further experiments, the information described in example 11, supra, was used to study and to analyze bovine neuroretina and murine 10 day embryos. Murine embryos were used because, apart from the general usefulness of the system for studying developmental biology, retinol dehydrogenases are extremely active in development. The model is extrapolatable to human development.

RNA (5–10 μg), was isolated from bovine neuroretinas, or from murine 10 day embryos, using well known techniques. The RNA was mixed in 4 μl of 5×AMVRT buffer, together with 4 μl of dNTPs from 5mM stock solutions, 2 μl of oligo dT (18mer, at a final concentration of 10 μM), together with 0.5 μl RNAse inhibitor, and 2 μl of avian myelostosis virus reverse transcriptase (10U). The final volume was 20 μl. This resulting mixture was incubated at 42° C. for 30 minutes, and then left on ice until used.

PCR was then carried out. In the PCR, two μl of cDNA were used. Primers were designed on the basis of the deduced amino acid sequence for bovine cDNA set forth supra. The following conserved amino acid sequences were noted:

```
A)  Cys Asp Ser Gly Phe Gly

B)  Pro Gly Trp Asp Ala

C)  Glu Ala Phe Ser Asp

D)  His Pro Arg Thr
```

"A" corresponds to amino acids 36–41 of SEQ ID NO:12. "B" is found at amino acids 283–287 of this sequence. "C" is found at positions 183–187, and "D" at positions 276–279. "Conserved" as used herein refers to conservation between the deduced sequence, the sequence for liver RDH shown by Chai, et al. J. Biol. Chem 270: 3900–3904 (1995), incorporated by reference in its entirety, and Simon, et al, J. Biol. Chem 270: 1107–1112 (1995), also incorporated by reference.

Degenerate oligomers were prepared. In a first set of PCR experiments, degenerate oligos based upon A and B were used as primers, i.e.:

5'-A C G T G A A T T C T G Y G A Y T C N G G N W T Y G G-3' (SEQ ID NO:16)

5'-A C G T G A A T T C T T N G C R T C C C A N C C-3' (SEQ ID NO:17) as forward and reverse primers respectively. The primers were mixed with the two μl of cDNA discussed supra. Conditions were 1 minute of denaturation at 94° C., 1 minute of annealing at 50° C., and two minutes at 72° C., for elongation. This constituted 1 cycle. Twenty-five cycles were carried out.

Following the first PCR, 5 μl samples of PCR product were combined with primers based upon "C" and "D," i.e.:

5'-A C G T G A A T T C G A R G C N T T Y T C N G A-3' (SEQ ID NO:18)

5'-A C G T G A A T T C C G N G T N C K N G G R T G-3' (SEQ ID NO:19) as forward and reverse primers, respectively. Conditions were exactly as used in the first set of experiments, except that the annealing temperature was 55° C.

Reaction products were analyzed on 1.5% agarose gels with ethidium bromide. The assumption was that the amplification products should be about 300 base pairs in length. As such, any 300 base pair bands visualized confirmed that the PCR protocol generated products of appropriate size. The experiments were repeated, using 1% low melting point agarose gels, and the PCR products were eluted therefrom. The isolated products were reamplified, using the same protocols, and were cloned into plasmids (TA cloning kit, Invitrogen). The plasmid DNA was prepared from transformants using standard protocols, and then analyzed by restriction digestion, using EcoRI. Any inserts of about 300 base pairs were analyzed further, using vector specific primers. The PCR products are presented in SEQ ID NOS: 20–23 with deduced amino acid sequences being presented as SEQ ID NOS: 24–27. SEQ ID NOS: 20 and 24 correspond to bovine sequences, while all others are murine sequences. In these nucleotide sequences, the first base ("C") is an artifact of the experiment, resulting from cleavage by a restriction endonuclease. Hence, one begins with the second nucleotide base in determining the deduced amino acid sequence. Further, note that sequences corresponding to the degenerate oligos, which would normally be included at the 5' and 3' termini, are not included.

EXAMPLE 13

The PCR product set forth in SEQ ID NO: 21 was then used in further probing experiments.

A murine 8.5 day cDNA library (in λgt10), was screened, using randomly labelled SEQ ID NO: 21, where the hybridization took place in 6×SSC, 0.5% SDS, 5×Denhardts's solution, 50% formamide at 42° C., with 100 μg/ml of salmon sperm DNA, followed by one wash at 2×SSC, 0.5% SDS at 50° C. for 30 minutes. A positive cDNA clone was identified, subcloned into pBluescript, and sequenced. The nucleotide sequence, and deduced amino acid sequence, are set forth as SEQ ID NOS: 28 and 29.

EXAMPLE 14

Following the work described, supra, the human cDNA was used to probe a human genomic library. The probe was prepared by PCR and randomly labelled as described supra. The primers used in the PCR were derived from the cDNA sequence of SEQ ID NO: 14 and were as follows:

Forward primer:

5'-G C T T C G G G C G C T G T A G T A-3' (SEQ ID NO:30) and

Reverse Primer:

5'-A A A A C A A T C T C T T G C T G G A A-3' (SEQ ID NO:31)

PCR was carried out by denaturing at 95° C., followed by annealing at 55° C., and elongation at 72° C. 2–5U of Taq polymerase and 0.2 µM of each primer were used. Thirty cycles were carried out.

The amplified fragment of 1056bp was isolated, following agarose gel electrophoresis analysis and cloned into vector PCR (commercially available from Invitrogen). This probe was used to screen a human genomic library in λFXII vector, from Stratagene. The manufacturer's instructions were followed to screen approximately $1 \times 10^6$ plaque forming units. $10^6$ cpm/ml of hybridization solution was used. Hybridization was carried out overnight with 6xSSC, 0.5% SDS, 5xDenhardt's solution, 50% formamide at 42° C., with 100 µg/ml of salmon sperm DNA, followed by one wash at 1xSSC, 0.1% SDS at 50° C. and a final wash at 0.5xSSC, 0.1% SDS at 65° C. Each wash was for 30 minutes. Several positive plaques were isolated, rescreened, and λDNA prepared, using the glycerol step gradient method described by Sambrook et al. Molecular Cloning, A Laboratory Manual (2d edition, 1989), incorporated by reference.

The isolated genomic clones were sequenced by analyzing fragments obtained following PCR reactions, using 100 mg of genomic λ clones per reaction as templates. To carry out the PCR, different primers, derived from the cDNA sequence of SEQ ID NO:11 were used in two PCR reactions, numbered 'one' and 'two'.

Specifically, the primers used in PCR reaction one were SEQ ID NO:30, supra (forward primer) and 5'-C T C A G G C T G T C A G A G A A G G C C T-3' (SEQ ID NO:32) (reverse primer)

The primers used in PCR reaction two were

5'-G A C G A T T T C C A G C G G G T G C-3' (SEQ ID NO:33) (forward primer) and

SEQ ID NO:31, supra

PCR was carried out by denaturing at 95° C., followed by annealing at 55° C. and elongation at 72° C. 2–5U of Taq polymerase and 0.2 µM of each primer was used. Thirty cycles were carried out. The amplified fragments from reactions one and two, were 2.2 kb and 2.5 kb respectively. Each fragment was cloned into vector PCR commercially available from Invitrogen.

Sequence analysis of the cloned fragments using vector specific primers or internal primers, permitted identification of exon-intron boundaries.

Figure 9:
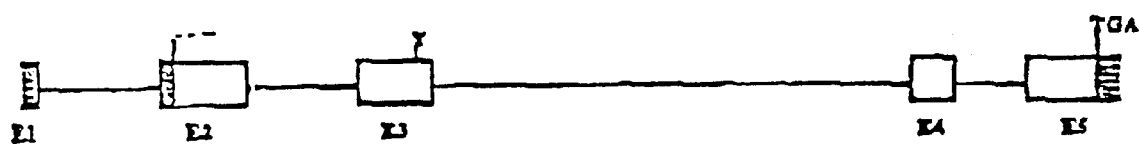
FIG. 9 shows the structure of the human 11-cis-retinol dehydrogenase gene.

The structure of the gene is presented in FIG. 9.

EXAMPLE 15

Studies were carried out to identify the location of the gene on chromosomes.

To do this, high molecular weight DNA was isolated from human leuckoytes, Chinese hamster cells, murine liver cells, and from hamster/human and mouse/human somatic hybrid cell lines. These hybrid cell lines each retained one human chromosome, as well as rodent genomes.

The isolated DNA was digested with Hind III, fractionated on agarose gel via electrophoresis, and then transferred to a nylon filter. These were then probed, using the human cDNA described supra, labelled as described supra.

Slides of chromosomes were prepared from lymphocyte cultures, using art recognized techniques. The λDNA from 3 genomic clones were mixed and labelled with biotinylated 16-dUTP, by nick translation. A centromere specific probe for human chromosome 12 centromere (obtained from the ATCC, under Accession Number D12Z1), was labelled with fluoro-red-dUTP, following the manufacturer's instructions. Pre-annealing of the probes, pretreatment of the slides, hybridization conditions, signal amplification, and detection, were in accordance with well known techniques. Chromosomes were counter-stained with 4,6 diamino-2-phenyl indole (DAPI), and signal was visualized using a fluorescence microscope.

Analysis of all of these data indicated that the gene which encodes the human form of p32 spans more than 4 kilobases, and is divided into 4 coding exons, which range from 165 to 342 base pairs in length. Further, an exon was found in the 5 untranslated region, and the length of the last coding exon has not been established. Introns range in size from 250 base pairs to 1.9 kilobases. FIG. 9 shows this schematically.

Study of exon/intron boundaries showed that all splice donor and acceptor sites follow the well known, canonical GT/AG rule. The Initiation codon and the conserved cofactor binding site are encoded by exon 2, while the active site, with invariant tyrosine residue, is encoded by exon 3. The gene maps to chromosome 12q13–14.

EXAMPLE 16

The work set forth in example 12 was extended, using the nucleic acid molecules set forth in SEQ ID NOS: 21 and 22.

A commercially available source of murine, multiple tissue Northern blots was used. Specifically, the nucleic acid molecules set forth in SEQ ID NOS: 21 and 22 were labelled with $^{32}p$, using standard methodologies. These labelled probes were then used to determine relative expression levels of transcript in murine tissue samples, using standard Northern blotting protocols. Blots were hybridized, overnight, at 42° C., using 50% formamide, 6xSSPE buffer, 0.5% SDS, 2xDenhardt's solution, 100 ug/ml salmon sperm DNA, and $1 \times 10^6$ cpm/ml of labelled probe. Blots were washed at room temperature, twice, for 30 minutes per wash, using 2xSSC and 0.1% SDS, followed by two further washes, at 50° C., in 0.1xSSC containing 0.1% SDS for 20 minutes. Blots were exposed at −70° C., overnight, using intensifying screens, and Kodak film. Abundant expression of a 1.4 kilobase transcript was observed by visual inspection as follows:

| | PROBE | |
|---|---|---|
| Tissue | SEQ ID NO: 21 | SEQ ID NO: 22 |
| Heart | − | − |
| Brain | − | ++ |
| Spleen | − | − |
| Lung | − | − |
| Liver | +++++ | +++++ |
| Skeletal Muscle | − | − |
| Kidney | +++ | +++ |
| Testis | − | − |

EXAMPLE 17

In view of the results of example 16, murine liver was used in the experiments which are described in this example. A murine liver cDNA library was prepared in λZAP, using standard protocols. Probes, as described in example 16, supra, were used to screen the library. Specifically, manufacturer's instructions were followed for plating the library and preparing the filters. Prehybridization was carried out at 42° C., in 50% formamide, 6×SSPE buffer, 2×Denhardt's solution, 100 ug/ml salmon sperm DNA. The filters were then hybridized, using 1×10^6 cpm/ml of hybridization-solution. Following overnight hybridization, filters were washed twice, in 2×SSC containing 0.1% SDS, (30 minutes per wash, at 52° C.), followed by two, 20 minute washes in 0.1×SSC containing 0.1% SDS, at 52° C. Filters were then exposed, as described supra. Any positive clones were rescreened, twice, until all plaques on a plate were positive. Inserts from several, positive clones were subcloned into plasmid pBluescript SK(+), using standard procedure by in vivo excision. Several of the resulting clone were sequenced.

When SEQ ID NO: 21 was used as a probe, three different cDNAs were identified. These are presented as SEQ ID NOS: 32, 33 and 34, herein. When SEQ ID NO: 22 was used, a full length clone, i.e., SEQ ID NO: 35 was found in one of the aforementioned plasmids. Amino acid sequences deduced therefrom are presented as SEQ ID NOS: 36–39, respectively. Proteins corresponding to SEQ ID NOS: 36–38 may have all trans activity,
5'-A C G T G G A T C C C C G C C T T C A T T C C G A A C A-3' (SEQ ID NO: 43) due to homology with known all-trans acting RDHs

EXAMPLE 18

The insert corresponding to SEQ ID NO: 35 was observed to be about 1.2 kilobases long. The actual sequence (1146 nucleotides) was close to this estimate. This clone was used in the experiments which follow.

The plasmid containing SEQ ID NO: 35 was linearized, using well known methods (BamHI endonuclease was used). Then, mRNA corresponding to SEQ ID NO: 35 was synthesized, using standard methods. The resulting mRNA was used, at 50 ng/reaction, in an in vitro translation system as described in the previous examples, in the presence of $^{35}$S. Microsomes were pelleted by centrifugation, and then subjected to SDS-PAGE analysis.

A band of about 34 kilodaltons was found in the in vitro translation product when priming with mRNA corresponding to SEQ ID NO: 35 was carried out. No such band was observed with non-primed microsome systems. These results demonstrate that the protein encoded by SEQ ID NO: 35 is a membrane associated protein having a molecular weight of about 34 kilodaltons, as determined by SDS-PAGE.

The hydropathy profile of the deduced amino acid sequence for SEQ ID NO: 35, i.e. SEQ ID NO: 39, was almost identical to that for known membrane associated 11-cis retinol dehydrogenases. Further studies were then carried out to determine the properties of this protein.

EXAMPLE 19

In order to generate a protein from a eukaryotic system, a 1.2 kilobase EcoRI fragment of the SEQ ID NO: 35 plasmid described supra was subcloned into a baculovirus expression vector, using known methods. Then, the vector was used to transfect Spodoptera frugiperda ("Sf9") cells, again using known methods. Recombinant baculoviruses were then amplified by several rounds of amplification, and were then used in fresh Sf9 cells. A parallel set of experiments were also carried out, but using recombinant virus containing an unrelated gene, whose expression product had no retinol dehydrogenase activity.

Expressed protein was then assessed for enzyme activity. In brief, membranes equivalent to 25 ug of total membrane protein from infected cells were incubated in phosphate buffered saline (PBS), containing 100 uM of 9-cis retinol, or all-trans retinol. Final volumes of incubated materials were 200 ul. Either cofactor NAD+ or cofactor NADP was also added, to a final concentration of 200 uM. The mixture was incubated for 20 minutes at 37° C., after which alkaline ethanol was added. The mixture was then extracted with 2.0 ml of n-hexane. The organic phase was then removed and dried under argon. Dried phases were dissolved in ethanol, and aliquots were analyzed by reversed phase HPLC, using a $C_{18}$ column, and a mobile phase of acetonitrile/water (85:15 v/v). Elution was at 1.0 ml/min, with effluent being monitored at 350 nm.

9-cis-retinaldehyde was one of the eluted products when NAD+ was present. Background levels 9-cis retinaldehyde were found with NADP which were comparable to the levels in mock infected cells. The mock infected cells also showed some 9-cis retinaldehyde, suggesting an endogenous, but not purified or characterized, 9-cis RDH. The cells which expressed the protein encoded by SEQ ID NO: 35 oxidized 9-cis retinol more than 8–10 times as efficiently as the mock cells.

In experiments not elaborated upon herein, 11-cis RDH activity was also observed for the protein, as was 13-cis RDH activity.

EXAMPLE 20

A series of experiments were then carried out to study the expression of SEQ ID NO: 35 in early mouse embryos.

Transcripts were taken from 9, 11, 13 and 15 day murine embryos, in the same way described supra. RT-PCR was then carried out, using the same conditions, as given supra, but in a two step procedure.

In the first step, a reaction was carried out using:
5'-T A G C T G G T A T C A T C G G G C C C A-3' (SEQ ID NO: 40) and
5'-A G A A A C C A G G C A G C A C T G G-3' (SEQ ID NO: 41)
while CRABPI transcripts were amplified using:
5'-C-A C G T G G A G A T C C G C C A G-3' (SEQ ID NO: 42) and ACGTGGATCC CCGCCTTCAT TCCCGAACA (SEQ ID NO: 43).
While glyceraldehyde-3-phosphate dehydrogenase (GAPDH) was amplified using:
5'-G G G T A T C G T G G A A G G A C T C A T G A C-3' (SEQ ID NO: 44) and
5'-A T G C C A G T G A G C T T C C C G T T C A G C-3' (SEQ ID NO: 45) respectively. Aliquots were taken, and then reamplified. In the second amplfication, SEQ ID NO: 41 was replaced by:
5'-G C T G G T C A C C T T C G T T A G T T C-3' (SEQ ID NO: 46)
Amplified bands were analyzed on a 1.5% agarose gel, and visualized with ethidium bromide. A 420 base pair band was indicative of the RDH encoded by SEQ ID NO: 35, while one of 210 bases was indicative of CRABPI, and one of 190 bases for GAPDH. The results indicated that the transcript was present during a large part of murine gestation.

Thus, as shown above, this invention provides a method for the isolation and characterization of retinol dehydrogenases, such as all-cis and all-trans retinol dehydrogenases which are membrane bound, may associate with components of retinol binding protein receptors, such as p63 of RPE cells and have a molecular weight of from about 30 to about 36 kilodaltons, as determined by SDS-PAGE. These enzymes have 9, 11, and 13-cis retinol dehydrogenase activity, and may have other properties inherent thereto. The primary structure of these proteins demonstrates that they have all the critical features of functional short-chain alcohol dehydrogenases, including a putative cofactor binding site and essential residues involved in the catalytic mechanism, namely the almost invariant tyrosine containing sequence motif Y-X-X-X-K (Persson et al., Eur. J. Biochem. 200:537–543 (1991)). The restricted tissue expression and the abundance of protein in RPE, such as p32 indicates that these proteins may carry out functions unique to the RPE. This possibility, and the fact that they can form complexes with p63, which previously has been shown to be a component of the retinoid uptake machinery in RPE-cells (Bavik, et al., J. Biol. Chem. 267:23035–23042 (1992)), shows that the substrate for the proteins is a retinoid. Wider tissue expression of short chain, alcohol dehydrogenase family members suggests that these molecules have additional functions.

A major metabolic step in retinoid metabolism in RPE-cells is the conversion of 11-cis retinol to 11-cis retinaldehydes. Based on the results obtained hereinabove showing the expression of the proteins in the RPE, and the particular biochemical properties of these proteins, further investigation confirmed that the proteins are in fact 9 and 11-cis-retinol dehydrogenases, which are enzymes which catalyze this reaction.

Thus, one aspect of the invention is the ability to produce recombinant 9 and 11-cis-retinol dehydrogenases. The recombinant enzyme can be used to produce 9 and 11-cis-retinaldehydes in levels higher, and in purer form, than would be available using standard biochemical methodologies. Thus, the isolated nucleic acid molecules of the invention, which include SEQ ID NO: 35, as well as those nucleic acid molecules which hybridize to SEQ ID NO: 10 under stringent conditions can be used in this context. By the term "stringent conditions" is meant hybridization in 6×SSC, 0.5% SDS, 5×Denhardt's solution at 68° C., with 100 ug/ml of salmon sperm DNA, and a final wash with 0.5–1.0×SSC at 50° C. The term is also used herein to refer to any set of parameters which are at least as stringent as those set forth above. As is well known, equally stringent conditions can be created by changing one parameter to make it less stringent, with another parameter being changed to increase its stringency. Thus, any nucleic acid molecule which fulfills the hybridization criteria set forth herein will be expected to code for a relevant cis-retinol dehydrogenase. The enzymes may be produced in an in vitro system, such as the one described above, or via transfecting or transforming eukaryotic or prokaryotic cell lines, such as CHO and COS cells, *Spodoptera frugiperda* or bacterial strains such as *E. coli* or the yeast strain *S.cervisiae* with the nucleic acid molecules of the invention. In an especially preferred embodiment, the nucleic acid molecules are contained within an expression vector, operably linked to a promoter. Complementary DNA, or "cDNA" is preferred, but genomic DNA and mRNA can also be used.

The identification of the retinol dehydrogenases, as members of the short-chain alcohol dehydrogenase superfamily is important in view of the retinoid-metabolism which occurs in non-ocular tissues. Studies show that generation of all-trans retinoic acid from all-trans retinol is carried out in a two step process (Posch et al., Biochemistry 30:6224–6230 (1991)). First, retinol is oxidized to retinal by a membrane bound retinol dehydrogenase. In a second step, the retinal is oxidized to retinoic acid. Thus, the oxidation of retinol into retinal, occurring in non-ocular tissues, is similar to the reaction carried out during synthesis of 11-cis retinal from 11-cis retinol in the visual cycle. In light of these similarities, it can be proposed that formation of all-trans retinal from all-trans retinol is carried out by an enzyme which is structurally similar to the retinol dehydrogenases of this invention. These findings are surprising in contrast to presently held views as it is generally believed that this metabolic step is carried out by members of the medium chain alcohol dehydrogenases. See Duester, Alcohol. Clin. Exp. Res. 15:568–572 (1991); Yang et al., Alcohol Clin. Exp. Res. 17:496 (1993) and Zgombic-Knight et al., J. Biol. Chem. 269:6790–6795 (1994). Thus the identification and structural characterization of the cis-retinol dehydrogenases, provided by this invention, also provide a previously unexpected avenue for the isolation and characterization of similar dehydrogenases involved in retinol metabolism is non-ocular tissues.

The proteins and nucleic acids encoding therefor and other aspects of this invention are also useful in many other important applications. For example, as it has been shown that p32 is part of an oligomeric protein complex which functions as a membrane receptor for RBP in RPE-cells, nucleic acid molecule encoding therefor can be used in a phenotypic/genotypic diagnostic analysis to determine retinoid accumulation, which can lead to retinitis pigmentosa.

Additionally, as shown, the proteins of the invention possess at least 9 and 11-cis-retinol dehydrogenase activity, which catalyzes the conversion of 9 and 11-cis retinol to 9 and 11-cis-retinaldehyde, the latter being a major metabolic step in retinoid metabolism in RPE-cells carried out by a membrane bound dehydrogenase. Thus, retinoid accumulation may be directly or indirectly tied to the presence of one or more of these proteins and/or its activation or inhibition, for example, complex formation with components of the RBP receptors p63, such as, but not only, p63 of RPE.

In other applications the effect of potential retinoid drugs for treatment of various diseases on the 9 and 11-cis-retinal dehydrogenase activity of the proteins of the invention may be assayed, as such drugs may adversely effect the enzyme, and to thus determine which of the different drugs have limited or no adverse effect on enzyme activity.

Examples of such diseases include those of the eye and also skin disorders such as psoriasis and acne. Certain cancers such as T-cell leukemias may also be tested by retinoid drugs and hence be candidates for assaying retinol dehydrogenase activity.

The various known functions of retinoids also suggests that various other retinoid linked pathological conditions may be diagnosed via assays for levels of the p63/cis-retinol dehydrogenase receptor complexes associated with a particular retinol binding protein. Art recognized techniques may be used, such a immunoassays, and so forth, to determine whether complex levels are too low or too high—i.e., are at variance with a normal level.

Further, as the cis-RDHs complex with the p63 component of the retinoid uptake machinery in RPE cells, they may also be used in a therapeutic context, as it is well known that soluble receptors may be used to prevent binding of a protein to its membrane-linked receptor. Thus, a subject characterized by enhanced levels of production of retinol binding protein may be treated via administering an amount of soluble receptor complex or antibody sufficient to inhibit binding of the retinol binding protein or other related molecule to its target, namely, an inhibitor of cis-retinol dehydrogenase activity. Other aspects of the invention will be clear to the skilled artisan and need not be repeated here.

In yet another application, monoclonal and polyclonal antibodies to these proteins can be generated, which are useful, inter alia, in monitoring the instance of pathological conditions characterized by aberrant levels of a receptor for retinol binding protein, by binding analysis of the antibody with body fluid or tissue samples. The generation of antibodies to the proteins of the invention can be accomplished, for example, by using the procedure set out in Bavik et al., J. Biol. Chem. 268:20540–20546 (1993) for the generation of antibodies to p63, including mAb A52.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. As isolated human or murine protein which has 11 cis-retinal dehydrogenase activity, a molecular weight of from about 30 to about 36 kilodaltons as determined by SDS PAGE, and is obtainable from retinal pigment epithelium (RPE) membranes.

2. The isolated protein of claim 1, which is a human protein.

3. The isolated protein of claim 1, having the amino acid sequence of SEQ ID NO: 15.

4. The isolated protein of claim 1, which also has 9 cis-retinol dehydrogenase activity.

5. The isolated protein of claim 1, which also has 13 cis-retinol dehydrogenase activity.

6. An isolated protein which has 11 cis-retinol dehydrogenase activity and a molecular weight of from about 30 kilodaltons to about 36 kilodaltons as determined by SDS-PAGE, having the amino acid sequence set forth in SEQ ID NO: 36, SEQ ID NO: 37, SEQ ID NO: 38, or SEQ ID NO: 39.

* * * * *